United States Patent
Bharat et al.

(10) Patent No.: US 10,290,098 B2
(45) Date of Patent: May 14, 2019

(54) SYSTEM FOR REAL-TIME ORGAN SEGMENTATION AND TOOL NAVIGATION DURING TOOL INSERTION IN INTERVENTIONAL THERAPY AND METHOD OF OPERATION THEREOF

(71) Applicants: KONINKLIJKE PHILIPS N.V., Eindhoven (NL); SUNNYBROOK HEALTH SCIENCES CENTRE, Toronto (CA)

(72) Inventors: Shyam Bharat, Arlington, MA (US); Ehsan Dehghan Marvast, New York, NY (US); Jochen Kruecker, Washington, DC (US); Ananth Ravi, Toronto (CA); Falk Uhlemann, Hamburg (DE); Cynthia Ming-Fu Kung, New York, NY (US); Thomas Erik Amthor, Hamburg (DE)

(73) Assignees: Koninklijke Philips N.V., Eindhoven (NL); Sunnybrook Research Institute, Toronto, Ontario (CA)

( * ) Notice: Subject to any disclaimer, the term of this patent is extended or adjusted under 35 U.S.C. 154(b) by 0 days.

(21) Appl. No.: 15/516,908

(22) PCT Filed: Sep. 30, 2015

(86) PCT No.: PCT/IB2015/057466
§ 371 (c)(1),
(2) Date: Apr. 5, 2017

(87) PCT Pub. No.: WO2016/059498
PCT Pub. Date: Apr. 21, 2016

(65) Prior Publication Data
US 2017/0301088 A1   Oct. 19, 2017

Related U.S. Application Data

(60) Provisional application No. 62/065,053, filed on Oct. 17, 2014.

(51) Int. Cl.
*A61B 5/00* (2006.01)
*G06T 7/00* (2017.01)
(Continued)

(52) U.S. Cl.
CPC .......... *G06T 7/0012* (2013.01); *A61B 5/4381* (2013.01); *A61B 34/20* (2016.02);
(Continued)

(58) Field of Classification Search
CPC ............... G06T 7/0012; G06T 7/10; G06T 2207/10132; A61B 5/4381; A61B 90/37
See application file for complete search history.

(56) References Cited

U.S. PATENT DOCUMENTS 9,392,960 B2    7/2016  Zvuloni et al.
10,092,360 B2 * 10/2018 Taylor ................... A61B 34/10
(Continued)

FOREIGN PATENT DOCUMENTS

WO    WO-2011161684 A2 * 12/2011 ......... A61B 10/0241

OTHER PUBLICATIONS

Shao, F. et al, entitled "Prostate Boundary Detection from Ultrasonographic Images," J. Ultrasound Med 22:605-623, 2003.

*Primary Examiner* — Brenda C Bernardi

(57) ABSTRACT

An interventional therapy system may include at least one controller which may obtain a reference image dataset of an object of interest (OOI); segment the reference image dataset to determine peripheral outlines of the OOI in the plurality image slices; acquire a current image of the OOI using an ultrasound probe; select a peripheral outline of a selected image slice of the plurality of slices of the reference image dataset which is determined to correspond to the current image; and/or modify the selected peripheral outline of the image slice of the plurality of slices of the reference image dataset in accordance with at least one deformation vector.

15 Claims, 9 Drawing Sheets

(51) Int. Cl.
*G06T 7/10* (2017.01)
*A61B 34/20* (2016.01)
*A61B 90/00* (2016.01)

(52) U.S. Cl.
CPC ............... *A61B 90/37* (2016.02); *G06T 7/10* (2017.01); *A61B 2034/2051* (2016.02); *A61B 2090/364* (2016.02); *A61B 2090/378* (2016.02); *G06T 2207/10132* (2013.01)

(56) References Cited

U.S. PATENT DOCUMENTS

| | | |
|---|---|---|
| 2010/0208963 A1 | 8/2010 | Kruecker et al. |
| 2010/0286517 A1 | 11/2010 | Kamen et al. |
| 2011/0178389 A1* | 7/2011 | Kumar .................. A61B 5/055 600/411 |
| 2012/0071758 A1* | 3/2012 | Lachaine ............... A61B 8/085 600/439 |
| 2013/0085383 A1 | 4/2013 | Fei |
| 2013/0102891 A1 | 4/2013 | Binnekamp et al. |
| 2013/0116548 A1 | 5/2013 | Kumar et al. |
| 2013/0197687 A1* | 8/2013 | Pavlovskaia ............ G06F 19/00 700/118 |
| 2013/0301893 A1 | 11/2013 | Netsch et al. |
| 2014/0078138 A1* | 3/2014 | Martin ................. A61B 8/0841 345/420 |
| 2015/0265354 A1* | 9/2015 | Stoianovici .......... A61B 5/4381 600/417 |
| 2017/0039776 A1* | 2/2017 | Endo ..................... G06F 19/321 |
| 2017/0224427 A1* | 8/2017 | Lavallee ................ A61B 34/20 |
| 2018/0114087 A1* | 4/2018 | Kamen ................. G06K 9/4628 |

* cited by examiner

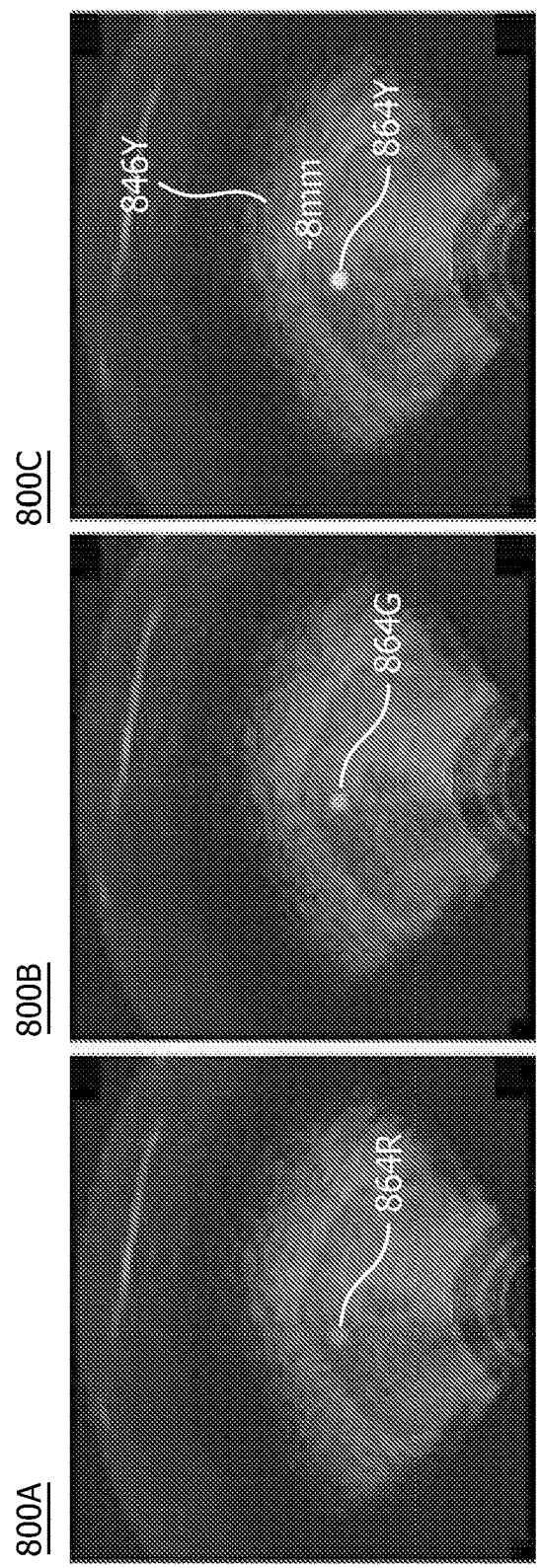

SYSTEM FOR REAL-TIME ORGAN SEGMENTATION AND TOOL NAVIGATION DURING TOOL INSERTION IN INTERVENTIONAL THERAPY AND METHOD OF OPERATION THEREOF

CROSS-REFERENCE TO PRIOR APPLICATIONS

This application is the U.S. National Phase application under 35 U.S.C. § 371 of International Application Serial No. PCT/IB2015/057466, filed on Sep. 30, 2015, which claims the benefit of U.S. Application Ser. No. 62/065,053, filed on Oct. 17, 2014. This application is hereby incorporated by reference herein.

FIELD OF THE PRESENT SYSTEM

The present system relates to an interventional therapy system and, more particularly, to an interventional therapy system for HDR brachytherapy with enhanced real-time tool guidance and real-time organ segmentation capabilities and a method of operation thereof.

BACKGROUND OF THE PRESENT SYSTEM

High dose rate (HDR) brachytherapy is a form of cancer therapy that utilizes high doses of ionizing radiation delivered over a short period of time (on the order of minutes) directly at or near a target.

In HDR brachytherapy of the prostate, hollow catheters are inserted via a template through the perineum of a patient and into the prostate of a patient, so that a segment of each catheter lies within the prostate of the patient. Care must be taken not to unnecessarily penetrate the bladder of the patient. Also, ensuring that the catheters are close to the boundaries of the prostate is an important clinical objective to reduce or minimize radiation dose to a central region of the prostate through which the urethra runs so as to reduce the likelihood of damage caused by the radiation to the urethra.

In a typical clinical workflow, the prostate boundaries are estimated subjectively and manually delineated by the clinician from pre-insertion transrectal ultrasound (TRUS) images. Therefore, the accuracy of inserting catheters close to the periphery of the prostate is highly dependent on the ability of the clinician to correctly and repeatedly identify the boundaries of the prostate (during catheter insertion), which are not always readily visible on TRUS images being provided to the clinician.

Sub-optimal catheter insertion can result in bladder punctures, uneven catheter distribution about the prostate, and catheters that are too close to the urethra the latter of which may adversely affect the dose coverage and/or increase radiation to normal tissue and/or structures in the vicinity of the prostate (e.g., the rectum) and is therefore undesirable.

SUMMARY OF THE PRESENT SYSTEM

The system(s), device(s), method(s), arrangements(s), user interface(s), computer program(s), processes, etc. (hereinafter each of which will be referred to as system, unless the context indicates otherwise), described herein address problems in prior art systems.

In accordance with embodiments of the present system, there is disclosed an interventional therapy system comprising at least one controller which is configured to and/or obtains a reference image dataset of an object of interest (OOI); segments the reference image dataset to determine peripheral outlines of the OOI in a plurality of image slices; acquires a current image of the OOI using an ultrasound probe; selects a peripheral outline of a selected image slice of the plurality of slices of the reference image dataset which is determined to correspond to the current image; and modifies the selected peripheral outline of the image slice of the plurality of slices of the reference image dataset in accordance with at least one deformation vector which may be formed in accordance with elastic deformation constraints. The controller may also be configured to select a cross-section of the reference dataset which is determined to correspond with the current image.

The interventional therapy system may further comprise a rendering device, wherein the controller further renders the current image with the selected peripheral outline of the selected image slice of the plurality of slices of the reference image dataset superposed thereon using the rendering device. Further, at least one sensor provides location information comprising position and/or orientation of the ultrasound probe when the current image was acquired. The controller may further be configured to select the selected image slice of the plurality of slices of the reference image dataset in accordance with the location information of the current image. The current image may comprise an image slice having a slice type selected from one of an axial or sagittal slice types and the image slices comprise a plurality of images of the same slice type as the current image.

The controller may further be configured to determine whether the modified selected peripheral outline of the image slice of the plurality of slices of the reference image dataset exceeds a threshold boundary change. In addition, the controller may further optimizes placement of catheters when it is determined that the modified selected peripheral outline of the image slice of the plurality of slices of the reference image dataset exceeds the threshold boundary change. The controller may also selects an image slice from the plurality of slices of the reference dataset which is determined to correspond to the current image.

In accordance with embodiments of the present system, there is disclosed a method performed by an interventional therapy system having an ultrasound probe, the method being performed by at least one controller of the interventional therapy system and comprising acts of obtaining a reference image dataset of an object of interest (OOI); segmenting the reference image dataset to determine peripheral outlines of the OOI in the plurality image slices; acquiring a current image of the OOI using an ultrasound probe; selecting a peripheral outline of a selected image slice of the plurality of slices of the reference image dataset which is determined to correspond to the current image; and modifying the selected peripheral outline of the image slice of the plurality of slices of the reference image dataset in accordance with at least one eformation vector.

In further embodiments, the method may further comprise acts of rendering, on a rendering device, the current image with the selected peripheral outline of the selected image slice of the plurality of slices of the reference image dataset superposed thereon; obtaining, from at least one sensor, location information comprising at least one of a position and an orientation of the ultrasound probe when the current image was acquired; selecting the selected image slice of the plurality of slices of the reference image dataset in accordance with the location information of the current image; forming the deformation vector in accordance with determined elastic deformation constraints; and forming the current image to comprise an image slice of a slice type selected from one of an axial or sagittal slice types, where the image slices comprise a plurality of images of the same slice type as the current image.

In accordance with embodiments of the present system, there is disclosed a non-transitory computer readable medium comprising computer instructions which, when executed by at least one processor, configure the at least one processor to control an interventional therapy system having an ultrasound probe, to perform acts of obtaining a reference image dataset of an object of interest (OOI); segmenting the reference image dataset to determine peripheral outlines of the OOI in the plurality image slices; acquiring a current image of the OOI using an ultrasound probe; selecting a peripheral outline of a selected image slice of the plurality of slices of the reference image dataset which is determined to correspond to the current image; and modifying the selected peripheral outline of the image slice of the plurality of slices of the reference image dataset in accordance with at least one deformation vector.

The computer instructions may further configure the at least one processor to render, on a rendering device, the current image with the selected peripheral outline of the selected image slice of the plurality of slices of the reference image dataset superposed thereon; as well as to obtain, from at least one sensor (108, 208, 940), location information comprising at least one of a position and an orientation of the ultrasound probe when the current image was acquired. The computer instructions may further configure the at least one processor to perform further acts described above in connection with the various embodiments of the performed methods and systems described above and further described in greater details below.

BRIEF DESCRIPTION OF THE DRAWINGS

The present invention is explained in further detail in the following exemplary embodiments and with reference to the figures, where identical or similar elements are partly indicated by the same or similar reference numerals, and the features of various exemplary embodiments being combinable. In the drawings:

FIG. 8A shows a screen shot of an estimated intersection of a catheter whose tip has not yet reached the current image plane superposed upon a current image in accordance with embodiments of the present system;

FIG. 8B shows a screen shot of an actual intersection point for a catheter whose tip has reached the current image plane superposed upon a current image in accordance with embodiments of the present system;

FIG. 8C shows a screen shot of an actual intersection point for a catheter whose tip has passed the current image plane superposed upon a current image in accordance with embodiments of the present system.

DETAILED DESCRIPTION OF THE PRESENT SYSTEM

The following are descriptions of illustrative embodiments that when taken in conjunction with the following drawings will demonstrate the above noted features and advantages, as well as further ones. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of well known devices, circuits, tools, techniques, and methods are omitted so as not to obscure the description of the present system. It should be expressly understood that the drawings are included for illustrative purposes and do not represent the entire scope of the present system. In the accompanying drawings, like reference numbers in different drawings may designate similar elements.

Figure 1:
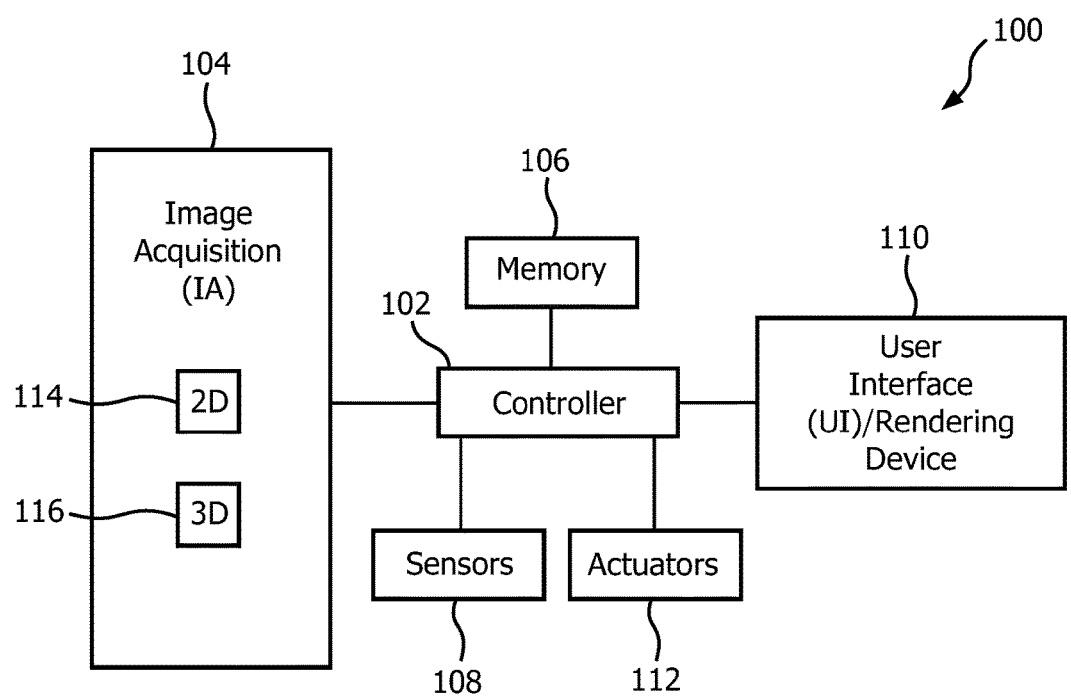
FIG. 1 shows a schematic of a portion of a system operating in accordance with embodiments of the present system.

FIG. 1 shows a schematic of a portion of a system 100 (hereinafter system 100 for the sake of clarity) operating in accordance with embodiments of the present system. The system 100 may include one or more of a controller 102, a memory 106, a user interface (UI) 110, actuators 112, sensors 108, and an image acquisition portion (IA) 104. One or more of the controller 102, the memory 106, the user interface (UI) 110, the actuators 112, the sensors 108, and the image acquisition portion (IA) 104 may be located integrally with, and/or remotely from, each other and/or may communicate with each other via any suitable wired and/or wireless communication methods. For example, in accordance with some embodiments, one or more or the controller 102, the memory 106, the user interface (UI) 110, the actuators 112, the sensors 108, and the image acquisition portion (IA) 104 may communicate with each other via a proprietary bus and/or a network as may be described elsewhere.

The controller 102 may control the overall operation of the system 100 and may include one or more logic devices such as processors (e.g., micro-processors, etc.), switches, gates, etc.

The image acquisition portion (IA) 104 may include two-dimensional (2D) imaging portion 114 and a three-dimensional (3D) imaging portion 116 which may capture 2D and/or 3D image information (generally image information), respectively. The 2D and 3D image information may be thereafter provided to the controller 102 for further processing and/or storage (e.g., in raw and/or processed form) in a memory of the system, such as the memory 106, for later use. For example, 3D image information may be acquired, processed, and thereafter stored in the memory 106 and 2D image information may be acquired in real-time and processed with the stored 3D image information in accordance with embodiments of the present system. The image acquisition portion 104 may include 2D or 3D imaging devices which may be suitable for a corresponding imaging application. For example, when imaging a prostate, the image acquisition portion 104 may include an ultrasound probe such as a transrectal-ultrasound (TRUS) probe or the like.

In accordance with yet other embodiments, other imaging modalities with real-time imaging capabilities such as an MRI may be provided to capture at least some image information of a desired organ or portion thereof. For example, in accordance with some embodiments, MR functional and anatomical imaging modalities may be provided and may be used to co-register functional data with anatomical features.

The 2D imaging portion 114 may include an ultrasonic imaging portion such as a TRUS probe or other suitable ultrasound probe to capture image information using ultrasound methods or the like. In accordance with some embodiments, the TRUS probe and may include separate axial and/or sagittal arrays.

In accordance with yet other embodiments, the TRUS probe may capture 3D image information. For the sake of clarity, and without limitation, embodiments of the present system may employ a TRUS probe. However, in accordance with yet other embodiments, other types of ultrasound probes may be substituted for the TRUS probe. In accordance with some embodiments, the TRUS probe may include an array to capture two-dimensional (2D) image information. Further, the array may be translated and/or rotated to capture three-dimensional (3D) image information. However, it is further envisioned that in accordance with some embodiments, the array probe may include a two-dimensional matrix to capture 3D image information. For example, the ultrasound probe may include any suitable array such as a one-dimensional array that may obtain image information for rendering a two-dimensional image. Further, in accordance with some embodiments, the array may be translated and/or rotated to obtain a three-dimensional image. However, in yet other embodiments, it is envisioned that the array may include a two-dimensional matrix array to obtain a three-dimensional image.

The 3D imaging portion 116 may include any suitable 3D imaging portion or portions such as a 3D TRUS probe which may be similar to or the same as the TRUS probe of the 2D imaging portion 114. However, the 3D imaging portion may include an image capture device such as a TRUS probe which may capture 3D information. For example, the TRUS probe may include a 2D TRUS probe which may be translated and/or rotated to acquire a 3D volume. The 3D imaging portion 116, may provide captured image information to the controller 102 which may reconstruct and thereafter store the reconstructed image information in a memory of the system, such as the memory 106, for later use. Accordingly, in accordance with some embodiments, the 3D TRUS probe may be provided with a rotation and/or translational stepper that may encode a spatial position of the 2D TRUS probe which may provide for reconstruction of an acquired 3D volume.

In accordance with some embodiments, it is envisioned that the 3D imaging portion 116 may include any suitable 3D imaging portion or portions such as an ultrasound imaging system, a magnetic resonance (MR) imaging (MRI) imaging system, and/or a computed tomography (CT) imaging system. In accordance with yet other embodiments, image information obtained from one or more imaging sources, such as a TRUS probe and/or an MRI, may be registered so as to provide a composite image, if desired.

The memory 106 may include any suitable non-transitory computer readable medium or memory device or devices which may be local and/or distributed. For example, in accordance with some embodiments, the memory 106 may include portions which may form a portion of a surface area network (SAN) which may be accessed by the controller 102 via any suitable network such as a local-area network (LAN), a wide-area network (WAN), the Internet, a telephony network, a proprietary network, etc. In accordance with yet other embodiments, at least a portion of the memory 106 may be located integrally within the controller 102. The memory 106 may store image information such as two-dimensional (2D) or three-dimensional (3D) image volumes of one or more objects-of-interest (OOIs) such as a prostate of a subject or patient (hereinafter the patient for the sake of clarity).

The sensors 108 may include one or more sensors which may detect a position and/or orientation of one or more desired portions of the system 100 such as positions of image capture devices (e.g., the TRUS probe or other image sensor(s)), a grid template, catheters, (e.g., implant catheters or portions thereof such as distal ends), the patient (or portions of the patient), etc. relative a desired reference frame and/or coordinate system (e.g., an x, y, z coordinate system). The sensors 108 may then form corresponding sensor information and provide this sensor information to the controller 102 for further processing. For example, the sensors 108 and/or controller 102 may determine a position and/or orientation of the TRUS probe 114 as it acquires an image using any suitable method or methods such as an electro-magnetic (EM) and/or optical tracking methods (e.g., optical shape sampling (OSS)). In accordance with some embodiments, the determined position and/or orientation of the TRUS probe 114 may then be associated with the corresponding image information. For example, a position and/or orientation of the TRUS probe may be obtained using an electro-magnetic (EM) field generator (FG) (EMFG) and/or an EM reference sensor or sensors which may form corresponding information indicative of a location of the TRUS probe 114.

Figure 2A:
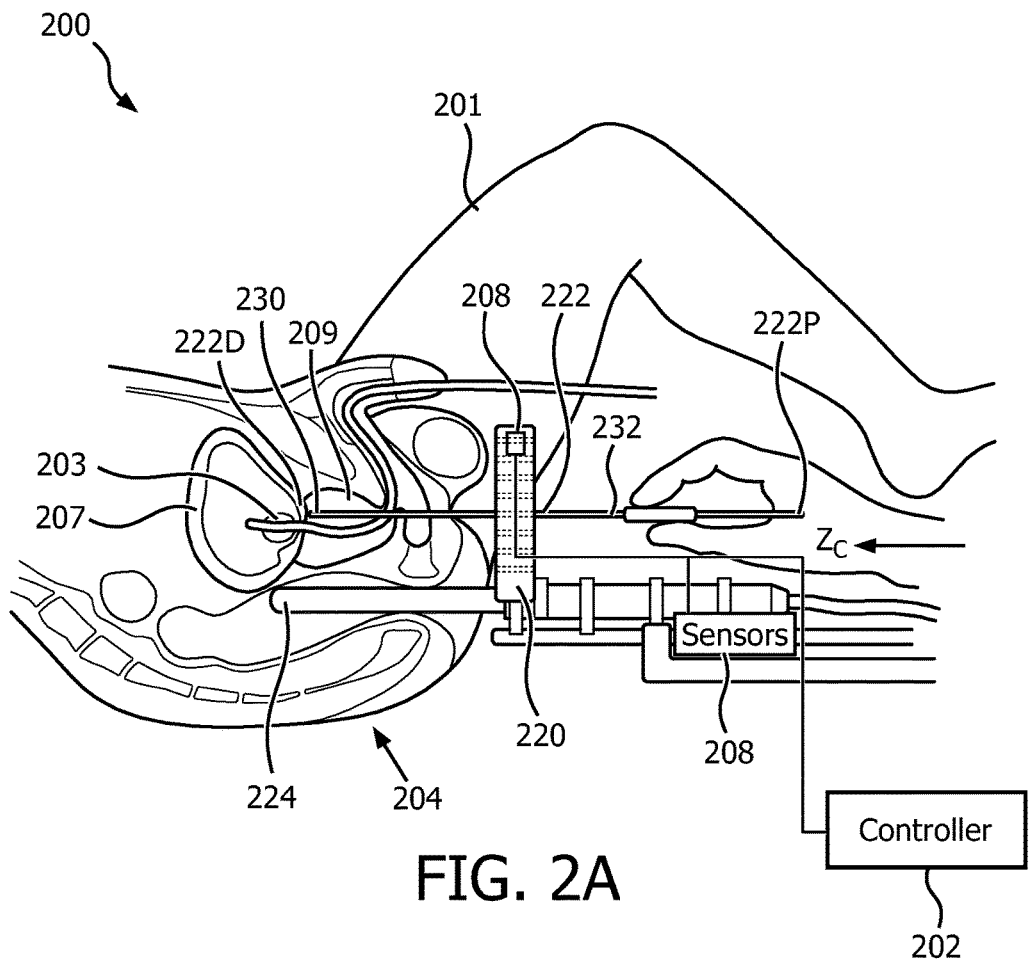
FIG. 2A shows a side view illustration of a portion of a system operating in accordance with embodiments of the present system.

For example, FIG. 2A shows a side view illustration of a portion of a system 200 operating in accordance with embodiments of the present system. The system 200 may be similar to the system 100 and may include an image acquisition portion 204, sensors 208, and a controller 202, which may be similar to the image acquisition portion 104, the sensors 108, and the controller 102 of the system 100, respectively.

The system 200 may further include one or more catheter assemblies 222 (hereinafter catheters for the sake of clarity) which may have proximal and distal ends 222P and 222D, respectively, and which may be supported and/or steered (at least partially) by a grid template 220. Without limitation, as one of more of the catheters 222 may be similar to each other, only a single catheter 222 may be discussed herein for the sake of clarity. Further, the catheters 222 may be steered by actuators controlled by the controller 202 and/or by a user, if desired. Similarly, the catheters 222 may be self inserted and/or retracted by actuators controlled by the controller 202 and/or by a user, if desired. The catheters 222 may be shaped and sized so that they may be inserted into a desired object-of-interest (OOI) such as a prostate 209 of a patient 201 such that a distal end of 222D of the corresponding catheter may be situated within the OOI while a proximal end 222P of the catheter may be situated outside of the OOI, during use. Without limitation, it is also envisioned that one or more of the catheters 222 may be the same as or different from each other, if desired.

Figure 2B:
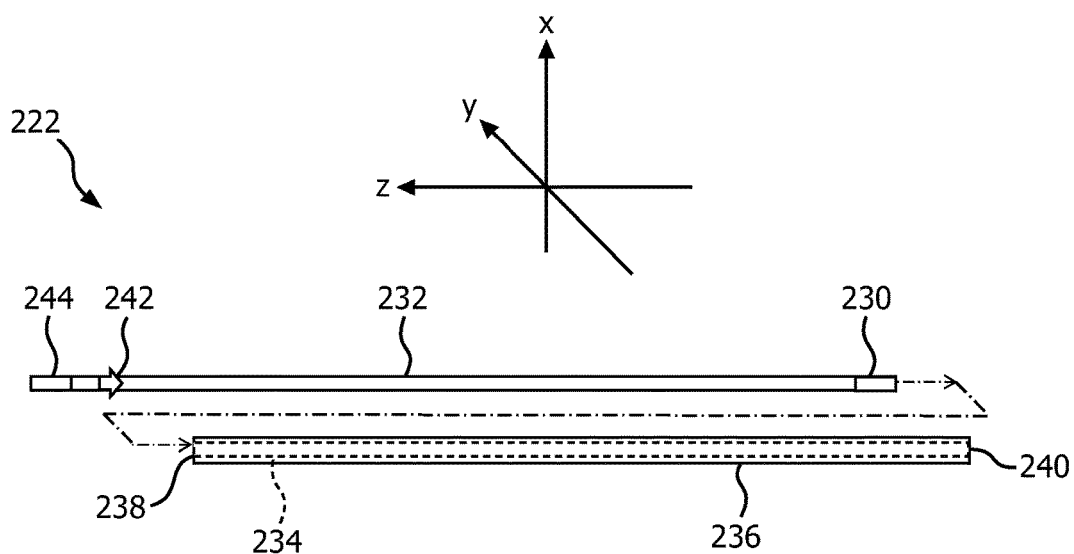
FIG. 2B shows an exploded view illustration of a catheter assembly in accordance with embodiments of the present system.

FIG. 2B shows an exploded view illustration of the catheter 222 in accordance with embodiments of the present system. Referring to FIG. 2B, the catheter 222 may be formed by an assembly including one or more of a body 236 and an obturator 232. The body 236 may include proximal and distal openings 238 and 240, respectively and a cavity 234 suitable to receive the obturator 232 situated between the proximal and distal openings 238 and 240, respectively.

The catheter 222 may include a tracking element such as one or more EM sensors 230 (e.g., EM tracking sensors) which may be tracked by the controller 102, 202 to determine position and/or orientation of the one or more EM sensors 230 and/or portions attached thereto. However, in yet other embodiments the tracking methods may include any suitable tracking method such as optical sensing (e.g., optical shape sensing) methods and/or the like.

Although the EM sensor 230 is shown attached to one end (e.g., a distal end) of the obturator 236, it is also envisioned that one or more EM sensors 230 may be attached to the body 236 such as at the tip of the body 236. Regardless the EM sensors 230 may be referred to as tracking elements. Moreover, in yet other embodiments, a plurality of tracking elements such as EM sensors 230 may be situated at various locations on the body 236 and/or the obturator 232 of the catheter 222 such as at their distal ends.

In accordance with some embodiments, the controller 202 may track (e.g., spatially track) the tracking elements using any suitable method such as an EM method and may determine location (e.g., position and/or orientation) of the tracking element and/or portion(s) of the catheter in close proximity to the tracking element. For example, during use such as during an HDR brachytherapy procedure performed in accordance with embodiments of the present system, the controller 202 may track a tip (e.g., a distal end) of the catheter 222 by determining a position and/or orientation of the tracking element located at the tip (e.g., the distal end) located at distal end of a corresponding obturator 232 of the catheter 222. In accordance with some embodiments, the controller 202 may detect the entry of a catheter 222 into a grid template. The controller 202 may further identify the catheter 222 (e.g., using an identification (ID) of the catheter) and/or may determine an array position within the grid template. This array position may provide coordinates of the catheter 222 in a desired plane (e.g., an x-y plane corresponding with a surface of the grid template, where a surface of the grid corresponds with z=0). As a catheter 222 passes through the grid template, its position within the grid template (e.g., col., row) may be determined. In accordance with some embodiments there a grid template may be optional. Accordingly, a user (e.g., a physician, clinician, etc.) may perform manipulate one or more of the catheters 222 implant the prostate by freehand.

The obturator 232 may be shaped and sized so as to be able to be slidably inserted into, and/or withdrawn from, the cavity 234 of the body 236 through one or more of the proximal and/or distal openings 238 and 240, respectively. However, in accordance with embodiments of the present system when performing HDR procedures, the distal opening 249 may be sealed using any suitable method such as by using an end cap situated at the distal opening 240 so as to seal the distal end opening 240. This may prevent accidental deposition of an HDR radioactive source (e.g., a seed) into the body of a patient. Accordingly, it will be assumed that obturator 232 may be inserted and/or withdrawn from the cavity 234 via the other opening (e.g., the unsealed opening) of the cavity 234 such as the proximal opening 238 of the body 236. The end cap situated at the distal opening may be shaped and sized (e.g., pointed, etc.) so that the catheter may easily penetrate tissue during insertion.

A holding mechanism may be provided to lock the obturator 232 in position relative to the body 236, if desired. For example, in accordance with embodiments of the present system, the holding mechanism may include any suitable holding mechanism such as a detent 242 which may engage portions of the body 236 so as to secure the obturator 232 to the body 236 for use. However, in accordance with yet other embodiments, the holding mechanism may include any suitable friction, screw, or latch type holding mechanisms or the like. For example, in accordance with some embodiments, the holding mechanism may include a wave-shaped feature or features (e.g., which may extend about an outer periphery of the obturator 232) so as to frictionally engage an interior portion of the cavity 234 of the body 236 when the obturator 232 is fully inserted into the body 236. This may prevent motion of the obturator 232 relative to the body 236 when maneuvering the combination. However, when a removal force is applied between the obturator 232 and the body 236, these portions may be separated from each other.

As discussed above, the obturator 232 may have a tracking element such as the EM sensor 230 located for tracking a location of the corresponding end. Accordingly, during use, the controller 102, 202 may determine a position and/or orientation of an end of the obturator 232 by determining a position and/or orientation of the corresponding tracking element such as the EM sensor 230 located at the corresponding end of the obturator 232.

Referring back to FIG. 2A, one or more of the catheters 222 may include a steering mechanism so that the catheters 222 may be actively steered by a user and/or the controller 202. For example, one or more of the catheters 222 may include actuators which may actively steer the catheters 222 or portions thereof such as the distal ends 222D under the control of a user and/or the controller 102, 202. For example, in accordance with some embodiments, the controller 202 may control the actuators of one or more of the catheters 222 to actively steer the distal end portion of the corresponding catheter 222 to (or in close proximity to) a desired position. The catheters 222 may be shaped and/or sized to be transplanted within the prostate 209 of the patient 201.

The image acquisition portion 204 may include an ultrasonic probe such as a TRUS probe 224 which may perform one or more scans and provide corresponding image information (e.g., 2D or 3D image information) to the controller 202 for further processing. The image information may further include information related to locations of portions of one or more of the catheters 222. For example, during implantation of one or more of the catheters 222, the TRUS probe 224 may provide transrectal ultrasound image information which may be provided to the controller 202 for further processing and may include information related to a position of one or more of the catheters or portions thereof, such as the distal ends 222D of the corresponding catheters 222. The controller 202 may then determine guidance information such as catheter guidance information in accordance with embodiments of the present system.

The sensors 208 may detect operating parameters, positions and/or orientation (e.g., relative to a desired reference point, points, reference planes, coordinates, etc.) of one or more portions of the system 200 such as positions of the catheters 222, the grid template 220, and/or the TRUS probe 224 and form corresponding sensor information which may be provided to the controller 202 for further processing in accordance with embodiments of the present system. In accordance with embodiments of the present system, sensors may track the position and/or orientation of the grid template 220, catheters position and/or orientation relative to each other and/or to the grid template 220, and/or position and/or orientation of the TRUS probe 224. In accordance with some embodiments, the sensors 208 may include EM and/or optical tracking sensors.

The controller 202 may process the image information in accordance with embodiments of the present system and render a composite image on a display of the system for the convenience of a user (e.g., a clinician, a doctor, etc). The controller 202 may further determine guidance information which may be determined by the controller 202 in accordance with embodiments of the present system. The guidance information may include information related to actual and/or desired (e.g., estimated) positions of one or more of the catheters 222 and/or portions thereof (e.g., a distal end of one or more of the catheters 222) relative to, for example, a fixed point, points, planes (e.g., the current live image plane), coordinates, potions of the system 200 (e.g., the grid template, etc.) and/or an object-of-interest such as the prostate 209. The guidance information may further include information related to actual and/or desired position(s) of the TRUS probe 224 or portions thereof relative to, for example, a fixed point, points, planes (e.g., along the z axis), or objects-of-interest (OOIs such as the prostate, etc.). For example, the controller 202 may determine guidance information such as probe guidance information (as opposed to catheter guidance information) which may indicate a desired location of the TRUS probe 224 along the z axis and render such information on a display of the system to inform a user of the desired location. However, in yet other embodiments, it is envisioned that the controller 202 may control actuators (e.g., probe location actuators) of the system to change the location of the TRUS probe 224 in accordance with the desired probe location information. Similarly, the controller 202 may determine catheter location information and control actuators of the system (e.g., actuators of the catheters and/or the grid template) to change location of one or more of the catheters 222 (or portions thereof) in accordance with the catheter location information. It is also envisioned that the controller 202 may render information related to the catheter location information on a display of the system for the convenience of the user. The probe and/or catheter location information may be determined and/or updated in real-time and may be rendered on a user interface of the system for the convenience of the user, if desired. The catheter guidance information may include desired positions of one or more of the catheters. The probe location actuators may form a portion of a TRUS probe positioning system which may position (e.g., using a stepper which may include a stepper motor, etc.) the TRUS probe 224 in a desired position relative to one or more coordinates under the control of the controller 202.

Figure 3:
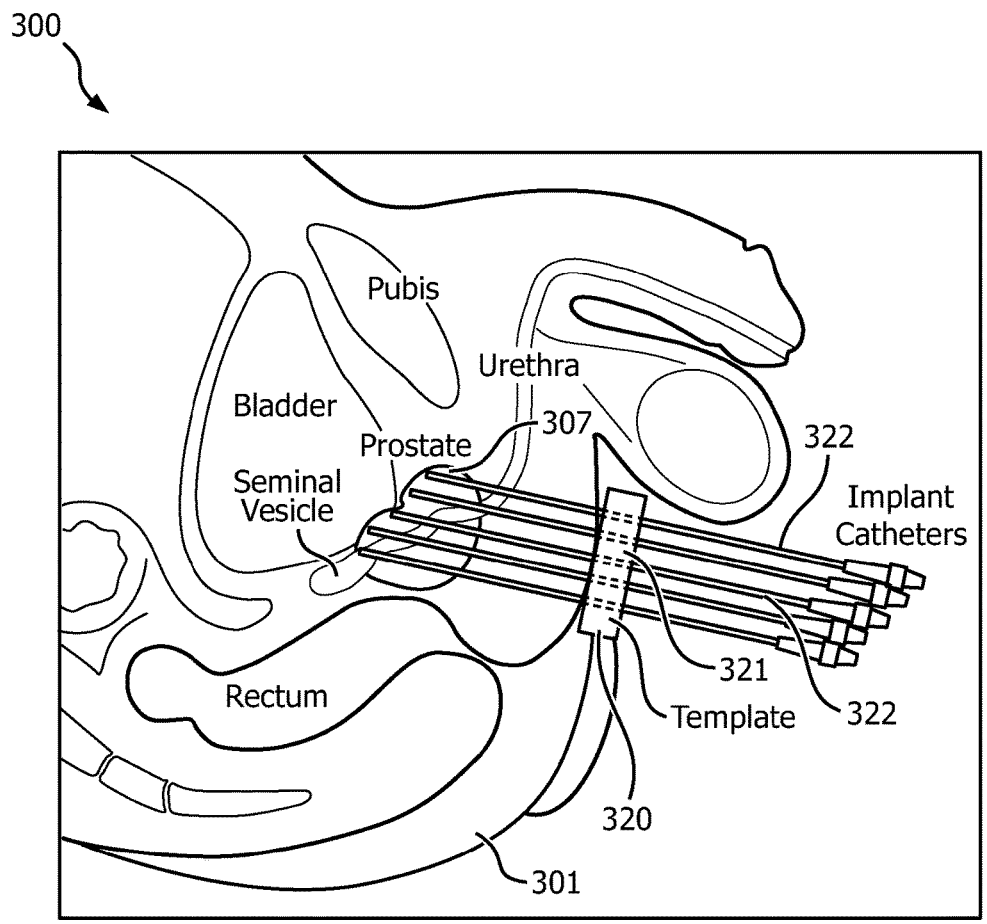
FIG. 3 shows a side view illustration of a portion of a system operating in accordance with embodiments of the present system.

A grid template positioning mechanism may be provided to locate the grid template 220 in a desired position and/or orientation. For example, FIG. 3 shows a side view illustration of a portion of a system 300 operating in accordance with embodiments of the present system. The HDR system 300 may be similar to the HDR systems 100 and/or 200 and may include catheters 322 and a grid template 320 which may be similar to the catheters 222 and the grid template 220 of FIG. 2A, respectively. The grid template 320 may include a plurality of channels 321 arranged in an array and which may be parallel to each other. The channels 321 may be shaped and/or sized to receive catheters 322 which may pass therethrough and may support and/or guide the catheters 322. Accordingly, the grid template 320 may provide an arrangement of catheters within a prostate 307 of a patient 301.

A grid template locating mechanism may adjust a position and/or orientation of the grid template 320 in relation to (e.g., about and/or along) one or more axes. In accordance with some embodiments, the grid template locating mechanism may be adjusted by a user (e.g., the clinician, etc.) so as to adjust a position and/or orientation of the grid template 320 in relation to one or more axes. However, in yet other embodiments, it is envisioned that the grid template locating mechanism may include at least one actuator which may adjust the position and/or orientation of the grid template 320 in relation to one or more axes under the control of a controller of the system 300. Further, the grid template locating mechanism may include sensors which may provide information related to position and/or orientation of the grid template 320 to the controller for further processing.

Referring back to FIG. 1, the actuators 112 may include one or more actuators which may be controlled by the controller 102. The actuators 112 may include for example, radial and/or linear motors (e.g., micro-electric motors (MEMs), electro-active polymers (EAPs), shape-memory alloys (SMAs), etc. which may output a desired force and/or displacement under the control of the controller 102 in accordance with embodiments of the present system.

The user interface (UI) 110 may include any suitable user interface which may render information for the convenience of the user. For example, the user interface (UI) 110 may include a display (e.g., a touch-screen display, etc.) a speaker, a haptic device, etc. Accordingly, the controller 102 may render information by providing this information to the user interface (UI) 110 which may then visually, audibly, and/or haptically output the information provided thereto. The user interface (UI) 110 may further include a user input device with which a user may enter information. For example, the touch-screen display may receive information entered by the user such as a user-selection, etc. In accordance with yet other embodiments, the user input device may include any other user input devices with which a user may enter information such as a mouse, a touch pad, a track ball, a stylus, etc.

Figure 4:
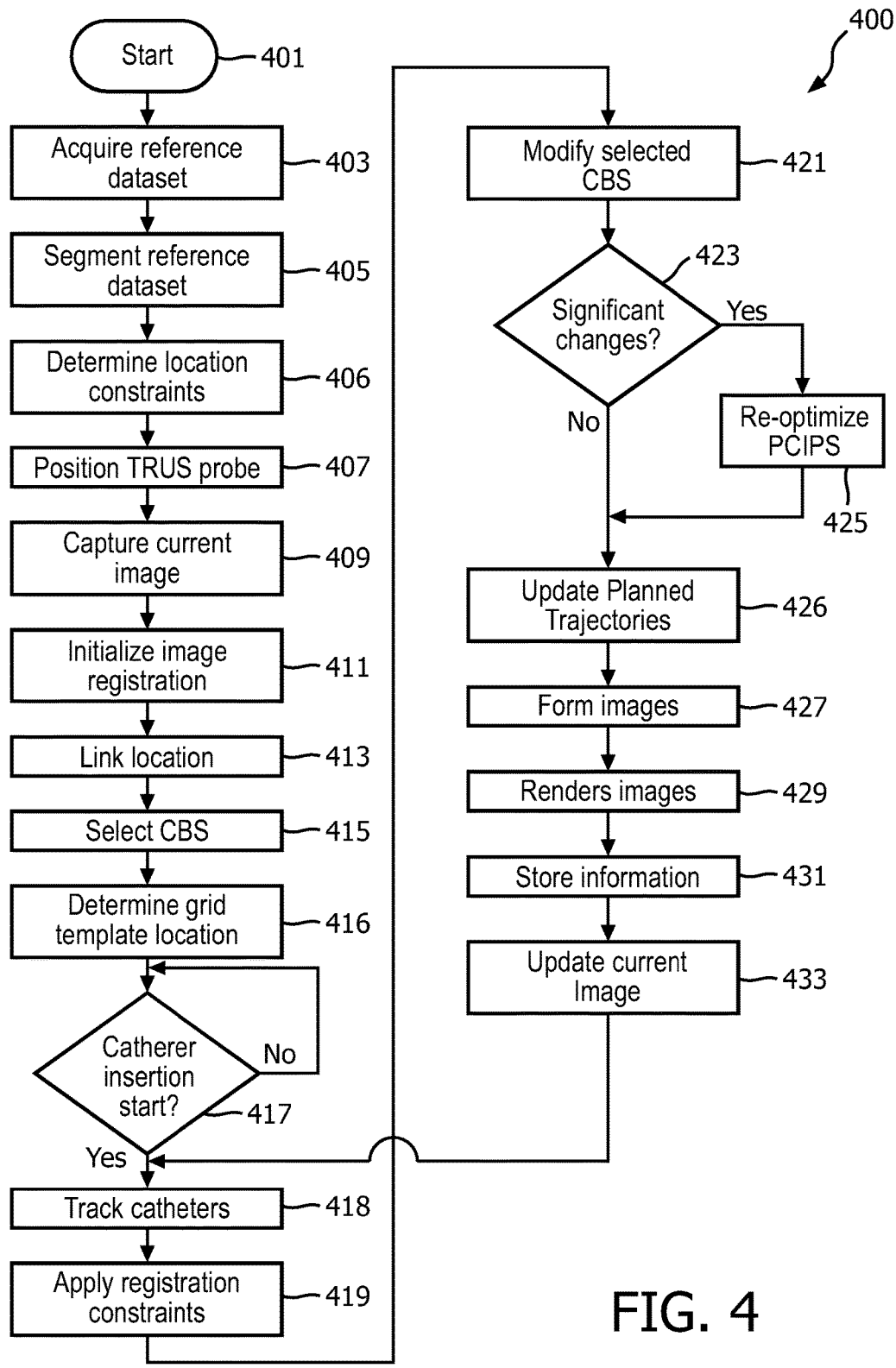
FIG. 4 shows a functional flow diagram of a process that may be performed in accordance with embodiments of the present system.

It is further envisioned that embodiments of the present system may provide a system and method to automatically segment boundaries of a prostate on a 2D image (axial or sagittal slice e.g., a current slice such as a 2D image slice) that may be rendered on a display of the system in real time. Accordingly, a clinician may be provided with quantitative knowledge of these determined boundaries on the current slice which may enhance a catheter insertion process. FIG. 4 shows a functional flow diagram of a process 400 that may be performed in accordance with embodiments of the present system. The process 400 may be used during interventional therapy procedures and may provide real-time guidance to a clinician or a catheter control system. The process 400 may be performed using one or more computers communicating over a network and may obtain information from, and/or store information to one or more memories which may be local and/or remote from each other. The process 400 may include one of more of the following acts. In some embodiments, the acts of process 400 may be performed using one or more suitable medical imaging systems such as ultrasound imaging systems or the like operating in accordance with embodiments of the present system. Further, one or more of these acts may be combined and/or separated into sub-acts, if desired. Further, one or more of these acts may be skipped depending upon settings. In operation, the process may start during act 401 and then proceed to act 403.

During act 403, the process may acquire a 3D reference image dataset of a volume-of-interest (VOI). The 3D reference image dataset (hereinafter reference dataset) may include a plurality (e.g., N, where N is an integer) of 2D image slices (hereinafter image slices) of the VOI in which a desired object-of-interest (OOI) such as a prostate of a patient may be located. Accordingly, the reference dataset may include N image slices of the desired OOI such as the prostate. These N image slices may be taken in one or more image planes. For example, in accordance with some embodiments, the image slices may be in the sagittal plane while in other embodiments the image slices may be in the transverse or other plane or planes. For the sake of clarity, rather than referring to the OOI throughout the description of process 400, reference will be made to the prostate. However, without limitation, it should be understood that the reference other OOIs may be substituted for the prostate, if desired. For example, it is envisioned that other organs and/or portions thereof may be substituted for the prostate if desired. However, reference is made to the prostate for the sake of clarity.

The reference dataset may be acquired using any suitable ultrasound imaging apparatus such as a TRUS probe or the like. However, in yet other embodiments other types of imaging devices are also envisioned and may be used with and/or substituted for the TRUS probe. During acquisition of the reference dataset, the imaging apparatus (e.g., the TRUS probe) may be tracked (e.g., by sensors of the system) so that a position and/or orientation of the TRUS probe may be determined and associated with each corresponding 2D image slice acquired. These image slices may then be stacked to form a 3D reference dataset.

In accordance with some embodiments, it is envisioned that the 3D reference dataset and/or portions thereof may be acquired using one or more imaging methods such as MRI, CT, MR, positron-emission tomography (PET), and/or ultrasound imaging methods. The acquired image information that may be obtained from multiple image acquisition sources may be registered to form all and/or a portion of the 3D the reference dataset, if desired. However, for the sake of clarity, it will be assumed that the 3D reference dataset is acquired using the TRUS probe described herein. Further, although embodiments of the present system may be described with respect to anatomical imaging and data methods, it should be understood that some embodiments imaging methods described herein may be similarly operative using functional imaging methods. For example, embodiments of the present system may translate functional information in real-time to provide a real-time guidance, if desired.

The TRUS probe may be located in a desired position and/or orientation relative to the patient. For example, FIG. 2A shows a setup of the TRUS probe 224 relative to the prostate 209 of the patient 201 so that it may acquire a reference dataset. The TRUS probe 224 may be tracked (e.g., along and/or about the z axis) during the acquisition of the reference dataset so that position and/or orientation of the TRUS probe 224 during acquisition of each 2D slice may be associated with the corresponding 2D slice of the 3D reference image dataset as location information. More particularly, the process may track the position and/or orientation of the TRUS probe, form corresponding location information, and associate this location information with corresponding 2D image slices of the reference dataset such as that shown in FIG. 5 which shows a flow diagram 500 of a process performed in accordance with embodiments of the present system.

Figure 5:
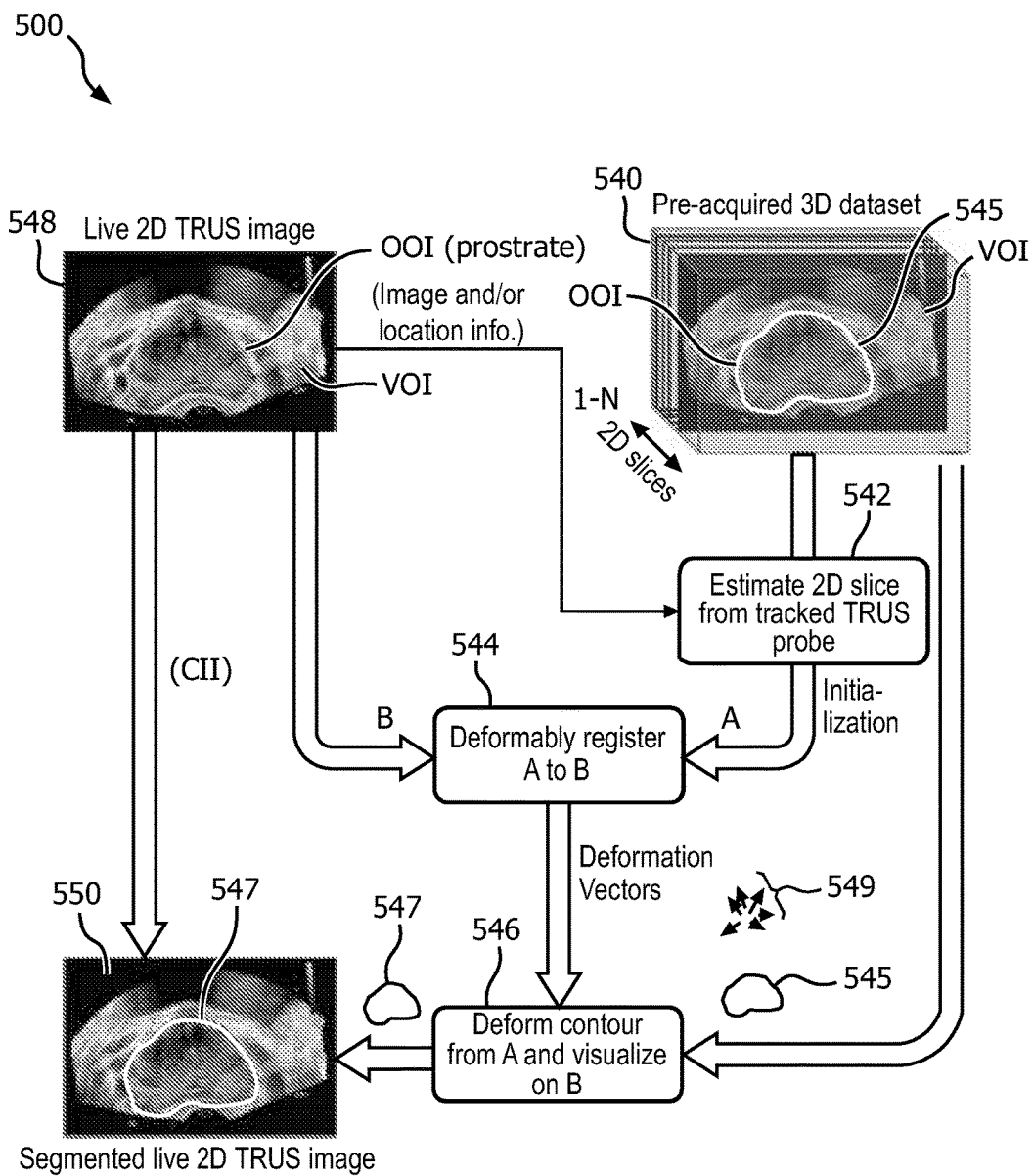
FIG. 5 shows a flow diagram of a process performed in accordance with embodiments of the present system.

More particularly, FIG. 5 shows a three-dimensional (3D) reference dataset 540 that may include a pre-acquired 3D image dataset having a plurality of (e.g., a selected number such as N) of two-dimensional (2D) image slices (e.g., 2D slices) taken of a VOI which may include the OOI, acquired prior to catheter insertion into the patient and stored in a memory for retrieval and referral during acquisition of further images using a catheter inserted into the patient. After completing act 403, the process may continue to act 405.

During act 405, the process may segment the reference dataset using any suitable segmentation method or methods which may include automatic and/or manual methods (e.g., using user input). For example, a suitable segmentation method may be provided using the UroNav™ fusion biopsy system (available with the UroNav™ biopsy platform; Invivo, Gainesville, Fla., USA), operating in accordance with embodiments of the present system, and may be performed to segment 3D image information in the reference dataset and form corresponding segmentation information (SI) which may define, for example, boundaries of portions within the VOI such as boundaries of the prostate for the 2D image slices of the 3D reference dataset. More particularly, embodiments of the present system may perform image intensity-based segmentation in a mid-gland transverse slice and then use this segmentation as an initialization to define the contours superior and inferior to this slice. Accordingly, the boundaries of the prostate may be defined for one or more of the image slices of the reference dataset and may be represented as curved boundary surfaces (CBSs) which may represent outlines of the prostate. More particularly, each of the plurality of 2D image slices (e.g., 2D image slices) of the reference dataset may be segmented to form segmentation information (SI) which may define the CBSs of the prostate. For example, with reference to FIG. 5, CBSs 545 may define the boundaries of the prostate for each of the plurality (or selected ones) of 2D image slices of the reference dataset 540. The process may associate the SI (which may include information related to the CBSs) with each corresponding 2D image slice of the 3D reference dataset and may store this information in a memory of the system for later use. Thus, the reference dataset may include the associated tracking and/or segmentation information.

In accordance with some embodiments, finite element analysis methods (FEA) may be used which utilize biomechanical models of tissue response to delineate biological tissue such as an organ and/gland so as to segment the reference dataset. Accordingly, it is envisioned that some embodiments may employ FEA methods to delineate the prostate within a 3D volume. Further, in accordance with yet other embodiments, gradient algorithms (e.g., as provided by MIM Software Inc., Cleveland, Ohio, USA) may be used to segment tissue and may define edges in addition to image intensity based segmentation. It is further envisioned that some embodiments may employ atlas based algorithms that use deformable registration to modify population based contours and apply them to the current dataset. After completing act 405, the process may continue to act 406.

During act 406, the process may define location constraints (LCs) such as at least one or more of planned catheter intersection points (PCIPs), peripheral boundary (PB) of the OOI, and restricted areas (RAs). One or more of the location constraints may be defined by the system and/or user. For example, in accordance with some embodiments, the process may determine PCIPs based upon at least one or more of the RAs and/or the CBSs. In yet other embodiments, a user may define one or more of the PCIPs and/or the RAs. In accordance with yet other embodiments, the RAs may be defined by the user and the PCIPs may be optionally defined. Further, in accordance with some embodiments, one or more of the location constraints may be determined based upon one or more other location constraints. For example, PCIPs may be determined based upon restricted areas and vice versa.

With regard to the PCIPs, the PCIPs for one or more catheters of the system may be defined relative to CBSs of the prostate as may be set forth in the segmented dataset. More particularly, the process may determine the PCIPs for one or more of the catheters relative to the boundary regions (e.g., peripheral boundary regions) of the prostate for one or more corresponding 2D image slices of the reference dataset as may be defined by the CBS. The PCIPs may be associated with corresponding 2D image slices and stored in a memory of the system for later use. More particularly, the PCIPs may be determined so that distal ends of one or more of the catheters are expected to be situated in the boundary region of the prostate (e.g., as defined by the CBSs which define the peripheral boundaries of the prostate) when the catheters distal ends are at their corresponding PCIP. Further, in accordance with some embodiments, the PCIPs may be further determined in accordance with restricted areas (RAs) as may be described below so that catheters do not intersect or otherwise touch RAs as will be described below. In accordance with some embodiments, the process may further determine PCIPS at least based upon the RAs. For example, the process may avoid PCIPs where their location may necessitate a catheter to pass through an RA. Thus, locations of a PCIP may be at least in part based upon the RAs which may be defined in the reference dataset.

The PCIP may generally define points that correspond with a position where a portion of a catheter such as a distal end (e.g., a tracked distal end) of one or more of the catheters is estimated (e.g., expected or calculated) to intersect with an image plane of a 2D image slice and may extend only a threshold extension value (as may be defined by the system and/or user) beyond the image plane (e.g., 0.5 mm, etc.). The process may perform this act using any suitable placement method or methods.

The process may render a user interface which may show the PCIPs for one or more catheters using any suitable method. For example, in accordance with some embodiments, the process may represent a catheter using a dot or other graphical representation.

In accordance with some embodiments, the process may determine catheter range which may generally be a difference between an actual location of a catheter (as may be measured at the tip of the catheter) and a current image plane or PCIP and provide a representation (e.g., alpha/numerical and/or graphical representation) of the result of the comparison for the convenience of the user. Catheter range will be discussed in further with respect to act 427.

Figure 6:
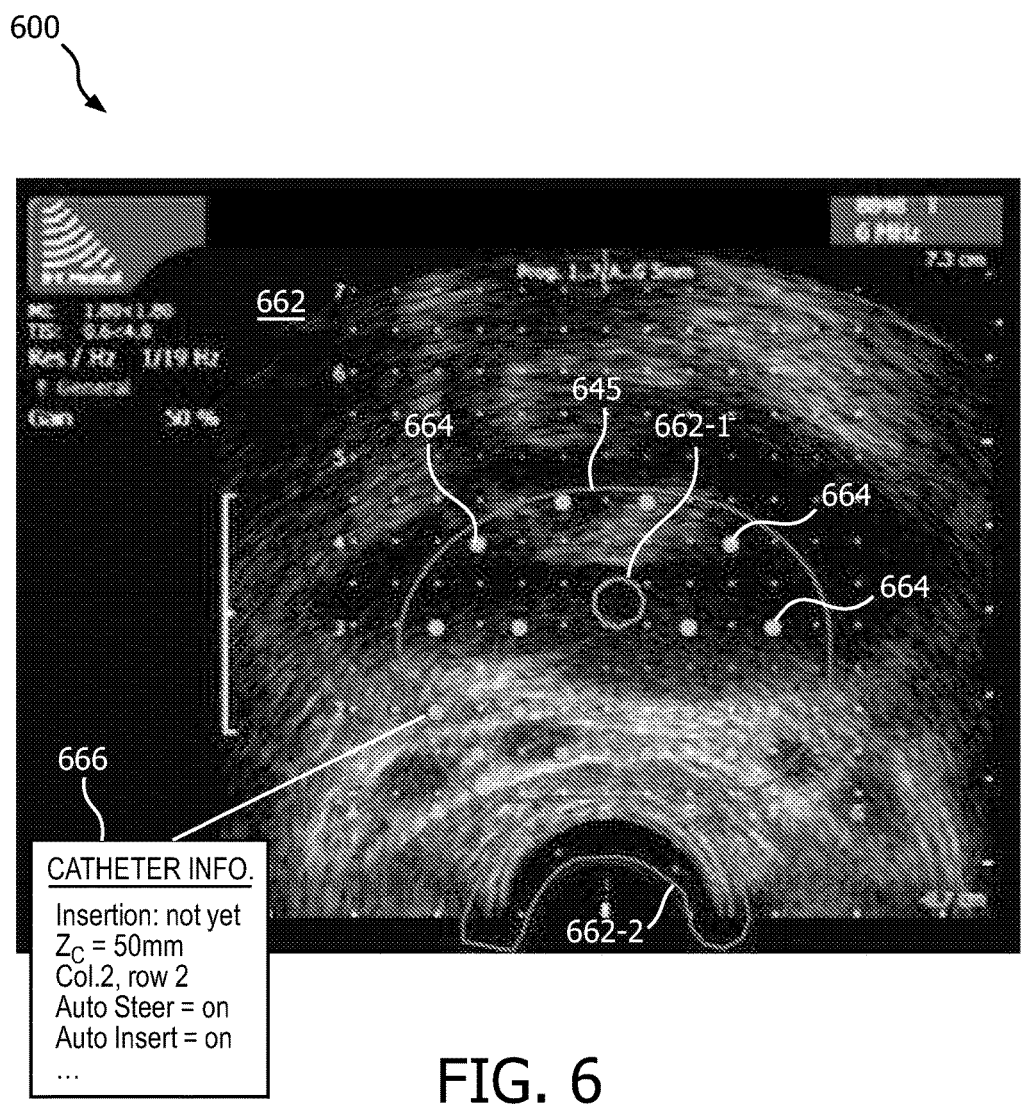
FIG. 6 shows a screen shot of a user interface (UI) illustrating planned catheter intersection points (PCIPs) superposed upon a corresponding 2D image slice of a reference dataset in accordance with embodiments of the present system.

Referring back to the location constraints, FIG. 6 shows a screen shot of a user interface (UI) 600 illustrating location constraints such as PCIPs 664 superposed upon a corresponding 2D image slice 662 of a reference dataset in accordance with embodiments of the present system. The CBSs 645 may be defined by the process and, thus, may be similar to the CBSs 545 of FIG. 5. However, in FIG. 6 the PCIPs 664 and restricted areas (RAs) are shown. The RAs may be illustrated by lines 662-1 through 662-M (generally 662-*x* superimposed upon corresponding 2D image slices 662 of the 3D reference dataset), where RAs 6621- and 662-2 are shown in FIG. 6 and may define areas through which none of the catheters should travel. The RAs may be distinguished as zones as will be discussed below. The system (e.g., during the segmentation) and/or the user may define the RAs. The RAs may be represented by any suitable shape such as lines which may set forth areas (e.g., on one side of the line) which are RAs and/or by using closed lines (e.g., a circle, a polygon, an ellipse, other custom-defined shapes, etc.) within which an RA may be located (as will be described below with reference to FIGS. 7A and 7B). Further, FIG. 6 may include a grid pattern (e.g., dots) which may be labeled 668 so that a user may easily determine location (e.g., col., row) of a catheter in an array of a corresponding grid template.

In accordance with some embodiments, a segmentation process may be operative to set RAs within the reference dataset in accordance with RAs set for one or more of the image slices. For example, if a user sets RAs in one image slice which define the boundaries of the urethra (e.g., a urethra zone), the process may automatically detect this and may determine RAs for the urethra zone in other 2D image slices of the 3D reference dataset. Thus, a user may set an RA (e.g., an RA for a zone) in an image slice of the reference dataset and the process may set this RA (e.g., the RA for the corresponding zone) throughout the reference dataset or a portion thereof.

Generally, travel through the RAs may be undesirable (e.g., travel of catheters in the vicinity of the urethra or bladder (shown in FIGS. 2-3 as 207 and 308) should be avoided so as not to cause physical damage to these structures) or impossible (e.g., through bones such as the pubic arch may be impossible unless drilled).

In accordance with embodiments of the present system, one or more types of RAs zones may be defined as shown in Table 1 below. The process may provide a user with a user interface to define the RA zones and may thereafter save information related to the defined RA zones as RA information in a memory of the system. Although, only three zones are shown, other zones may be defined and stored in a memory of the system for later use. Further, different RA zones may be defined for different procedures. For example, other types of HDR procedures may each have corresponding RA zones defined which may, for example, differ from the RA zones of Table 1.

TABLE 1

Restricted Areas

| Zone (Area) | Description of Zone |
|---|---|
| Urethra | The urethra itself (plus a threshold margin around it, if desired) |

TABLE 1-continued

Restricted Areas

Figure 7A:
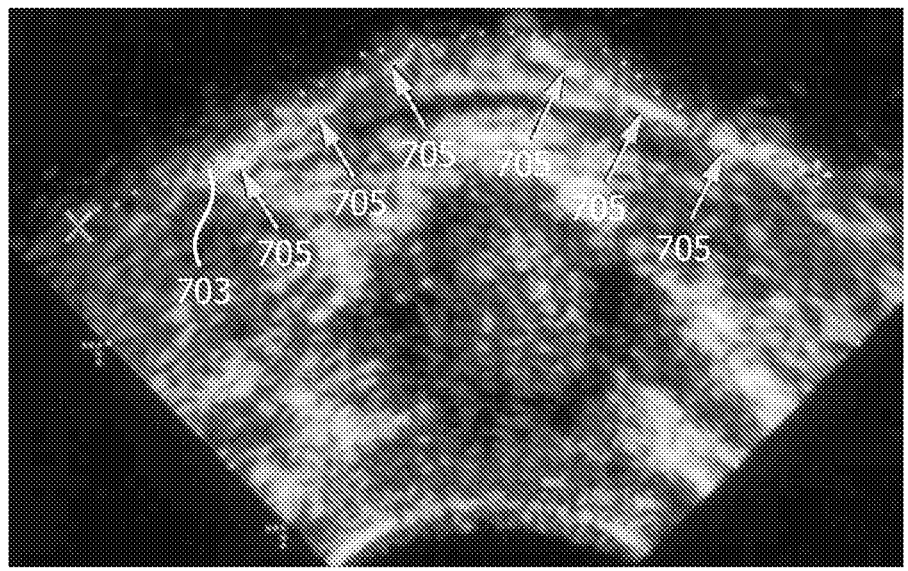
FIG. 7A shows a screen shot of a user interface (UI) illustrating a 2D image slice including a pubic arch of a reference dataset in accordance with embodiments of the present system.
Figure 7B:
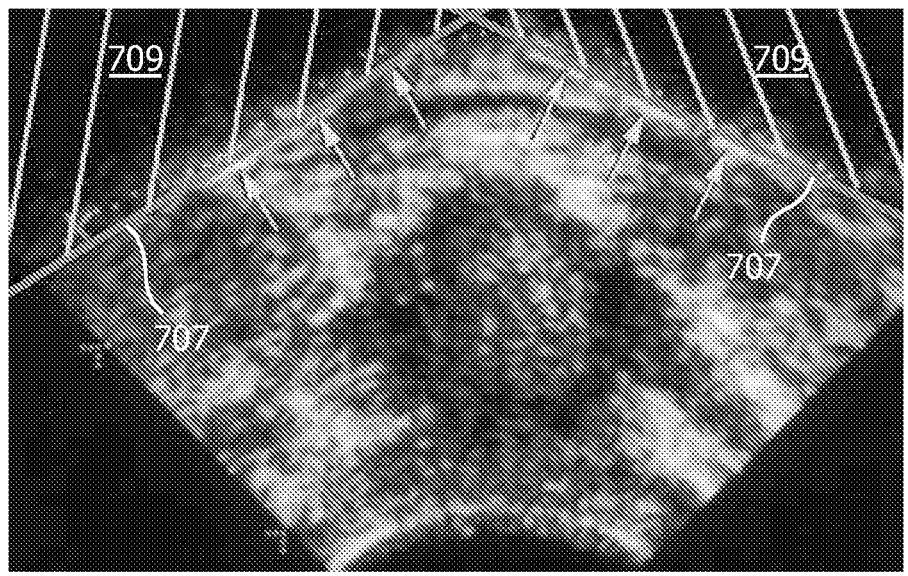
FIG. 7B shows a UI illustrating the 2D image slice after segmentation and selection of a pubic arch RA in accordance with embodiments of the present system.

| Zone (Area) | Description of Zone |
|---|---|
| | A vertical band throughout the entire workspace, containing the urethra segmentation (plus a margin around it, if desired) |
| Bladder | The bladder itself (plus a margin around it, if desired) |
| Rectum | The rectum (e.g., see, 662-2) (plus a threshold margin around it, if desired) |
| . . . | . . . |
| Pubic arch | The pubic bone (plus a threshold margin around it, if desired) May be defined by lines (e.g., pubic arch lines) that may indicate the location of the pubic bone (see, FIG. 7B). The entire workspace above (e.g., anterior to) the 2 lines 707 may be defined as a (pubic arch) RA. |

One or more of the RAs (e.g., of an RA zone) may be segmented automatically by the process during segmentation and/or after segmentation by a user. For example, the in accordance with some embodiments, the Urethra zone may be selected by the process during segmentation (e.g., see, 662-1, FIG. 6) while a Pubic arch zone may be selected manually. For example, FIG. 7A shows a screen shot of a user interface (UI) 700A illustrating a 2D image slice including a pubic arch of a reference dataset in accordance with embodiments of the present system; and FIG. 7B shows a UI 700B which is the UI 700A illustrating the 2D image slice after segmentation and selection of a pubic arch RA in accordance with embodiments of the present system. Referring to FIG. 7A, a location of the pubic arch is illustrated by a path shown by dotted line 703 and is pointed to by arrows 705. This path (e.g., path 703) may be segmented by the process automatically, if desired or may be set by a user. Referring to FIG. 7B, the process may provide the user with an option to enter and/or edit Pubic arch lines 707 that may define the Pubic arch of the Pubic bone. The process may then set an entire workspace above (e.g., anterior to) the Pubic arch lines 707 as a pubic arch RA. The process may then highlight (e.g. via cross hatching) the Pubic arch RA (zone) using any suitable method such as by inserting cross hatching 709 into the pubic arch RA. A user may then modify a position of the pubic arch lines 707 in real time, if desired and the process may update the pubic arch RA accordingly. However, in accordance with some embodiments, the process may form the pubic arch RA automatically during segmentation of the reference dataset and may then render information related to the pubic arch RA so that a user may approve, edit, and/or reject the pubic arch RA. Although, the pubic arch RA is discussed, the process may perform similar acts to select other RAs, as may be desired.

Referring back to the PCIPs, the process may determine and/or optimize the PCIPs in accordance with the RAs as may be set by the system and/or user. For example, after the PCIPs are determined that process may render this information for the convenience of the user. The user may then set the RAs and the process may then optimize the PCIPs in accordance with the set RAs. Accordingly, if the PCIPs are not near, for example, the Urethra, a user may determine that there is no need to set Urethra RAs. This may save time if desired. However, in accordance with some embodiments, it is envisioned that PCIPS may be determined and RAs set automatically without user intervention for the reference dataset.

After completing act 406, the process may continue to act 407 during which the TRUS probe may be positioned at a desired position for a catheter insertion process in which one or more of a plurality of catheters may be inserted into the prostate. The TRUS probe may be automatically positioned by a controller of the process into a default position and/or orientation such as with the transverse/axial array set to image the mid-gland region of the prostate of the patient or may be manually positioned by a user such as a clinician.

For example, in accordance with some embodiments, after it is determined that the reference dataset has been acquired, the process may render information informing the user to place the TRUS probe in position (e.g., a start position) so that the TRUS probe may acquire images of the prostate as will be described below. However, in accordance with yet other embodiments, the process may control actuators of the system to locate the TRUS probe in the desired position and/or orientation such as a default start position. The default start position may be selected from a default value obtained from a memory of the system and/or determined in accordance with a start position determined in accordance with a start position of the TRUS probe when acquiring the reference dataset. In accordance with yet other embodiments, the process may request a user to position the TRUS probe in a desired position and thereafter may automatically control position and/or orientation of the TRUS probe. After completing act 407, the process may continue to act 409.

During act 409, the process may capture a current image (e.g., in 2D) of the VOI which includes the prostate in real time and may form corresponding image information. Thus, the current image may be considered a live image. The current image may be updated at a desired frame rate (e.g., 15 frames-per-second in the present embodiments). In accordance with yet other embodiments, the current image may be updated (e.g., by repeating act 409) after one or more acts of the current process are completed. The current image may be dependent upon a location of the TRUS probe. Position of the TRUS probe may be based upon a user's selection, if desired and may, for example, include a mid-gland position.

In accordance with yet other embodiments, the current image may be updated when certain conditions are determined to occur such as when a position of the TRUS probe is changed, upon detecting a user's request, upon detecting insertion of a catheter or subset of catheters into the prostate, or detecting a user- or system-defined condition such as detecting that movement of an advancing catheter is stopped for a threshold period of time (e.g., 5 seconds) or advanced a certain amount in a desired direction as may be set by the user and/or system.

Referring to FIG. 5, the current image may include a live 2D TRUS image 548 which may be acquired by the TRUS probe and which may include the prostate.

In accordance with other embodiments, it is envisioned that the current image (e.g., live or intra-procedural image) may be captured as 3D image information using a 3D probe. Accordingly, the 3D image information may then be processed similarly to the 2D image: It may be displayed, with surface or volume rendering, or using one or more 2D cross-sections through the 3D volume. Further, it is also envisioned that the segmented reference dataset may be used to initialize a segmentation in the current image, enabling real-time segmentation and visualization of the intra-procedural organ boundaries, and/or of any RAs, if desired. The process may further select a default image slice from the current image and set this slice as the current image, if desired.

In accordance with yet other embodiments, the user- and/or system-defined conditions may be set by the user and/or system as desired using, for example, a settings table formed and/or rendered by the process. Accordingly, a user may interact with the settings table to set/reset the settings table so as to define user-defined conditions, if desired. Thereafter the settings table may be updated correspondingly and stored in a memory of the system for later use. The process may then obtain the settings table from a memory of the system and, when settings as defined in the setting table are determined to occur, the process may perform corresponding acts such as updating the current image.

The process may further track the TRUS probe to determine its position and/or orientation and form corresponding location information which may include position and/or orientation information of the TRUS probe and may associate the TRUS probe location information with the current image. In other words, the process may associate the location information, which may include information related to position and/or orientation of the TRUS probe when the current image was acquired, and associate this information with the corresponding current image. In accordance with some embodiments, the current image and the associated location information may be stored in a memory of the system for further processing, if desired.

In accordance with some embodiments, the process may provide a user with an option to select an image plane in which to view the current image such as in the axial and/or sagittal image planes. The process may then segment the 3D image set in accordance with the selected image plane. For example, if it is determined that the user has selected the sagittal image plane, then the process may segment the reference dataset in the same plane. Similarly, if it is determined that the user has selected the axial image plane, then the process may segment the reference image dataset in the same plane. However, in accordance with some embodiments, the process may segment the reference dataset in both planes and may then select images in a plane which corresponds with the plane that is selected for the current image. Thus, if the current image is selected in the axial plane, the process may obtain the segmented images which correspond with the axial plane of the reference image dataset. Thus, the current image may be obtained in the same reference plane as the image slices. After completing act 409, the process may continue to act 411.

During act 411, the process may initialize an image registration process. Accordingly, the process may select at least one image slice (e.g., 2D image slice) of the reference dataset which is determined to be a best fit (e.g., a closest fit) to the current image. In other words, the process may estimate at least one of the (2D) image slice(s) (e.g., in the corresponding axial or sagittal planes) from the reference dataset, that best matches the current image in accordance with the location information.

The selected image slice may be selected from the reference dataset and may have a location which most closely matches a location of the current image. Accordingly, the process may determine a location of the current image (e.g., based upon location of the TRUS probe) along a predetermined axis (e.g., the z axis as determined by a location of the TRUS probe) and may then select the image slice from among the image slices of the reference dataset that corresponds (or most closely corresponds) with the location of the current image (e.g., along the same axis and in the same plane) The selected image slice may be considered a best-fit image slice by location.

For increased robustness, the process may determine whether the selected image slice is a closest match to the current image using any suitable method such as using any suitable image analysis method. If the selected image slice is determined not to be a closest match, the process may select an image slice from the reference dataset that is closest (e.g., by ±ns slices, where ns is an integer) match to the current image. Further, when performing the image analysis, the process may take into account that the current image may include interventional tools such as the catheter, etc., in addition to the prostate. Accordingly, the process may filter the interventional tools when comparing the current image with image slices of the reference dataset. In accordance with some embodiments, the process may select two closest image slices from the reference dataset that most closely match the current image and may then form a selected image slice as a composite image based upon the two selected closest image slices.

With regard to patient motion relative to the TRUS probe between acquisition of the reference dataset and the current image, little motion is expected and is not expected to impact a workflow of the current process. More particularly, as the TRUS probe may fit tightly within a rectum of the patient, little relative probe motion is expected in the lateral and/or A-P directions. This motion may be generally be considered to be insignificant.

The process may perform this act using any suitable image matching method such as a method provided by the UroNav™ biopsy platform operating in accordance with embodiments of the present system. This is illustrated with reference to act 542 of FIG. 5.

In accordance with some embodiments, to increase robustness, the process may select at least two image slices (e.g., an image set) from the reference dataset that most closely matches the current image±ns slices (where ns is an integer such as 1 and may be set by the user and/or system), rather than selecting a single image slice from the reference dataset. This process may be used if reference dataset was acquired using the same slice orientation as the current image. Accordingly, location information may be used to select a range of image slices (e.g., the image set) from the reference dataset by location. The process may then form a composite image based upon the image set and set this composite image as a selected image. The process may further determine a CBS for this image. In yet other embodiments, the process may apply image matching to select one or more images from the image set and set. The process may then form a composite image (e.g., if two or more images are selected from the set as discussed above). The process may further use any suitable method to determine a corresponding location (e.g., via interpolation, etc.) for the composite image. Thus, for example, if the process forms the composite image based upon two images from the reference dataset that are respectively located at ±1 mm (along the z axis), the process may determine that the location for the composite image is 0 mm (along the z axis). As discussed above, multiple images may be used to overcome any possible relative patient-probe motion, if desired. The process may store the selected image slice (if a composite image) in association with the reference dataset for later use. The process may further determine a CBS for the composite image as discussed above and may store the CBS in association with the composite image in the reference dataset for later use. The composite image may be referred to as a pseudo image.

In yet other embodiments, the selected image slice (e.g., 2D image slice) may be selected from the reference dataset as an image slice which is determined to be a best fit (e.g., a closest fit) to the current image using only image analysis methods rather than by location as discussed above, if desired.

Further, in accordance with yet other embodiments, the reference dataset may include any 3D dataset and may not even include well-defined image slices or may include image slices which may have a different orientation from the current image. Accordingly, in this case, the process may determine a volumetric slab within the reference image dataset (e.g., having any suitable thickness such as 5 or 10 mm thickness, etc.) within which the current (e.g., live) 2D image may be located. A 2D cross section at any location within this slab could then be used to initialize the live 2D segmentation, and some metric of "goodness of segmentation" may be used to select the best 2D segmentation. The segmentation within the above-described slab may be used to constrain the current 2D segmentation, if desired.

After completing act 411, the process may continue to act 413.

During act 413, the process may link the location of the current image with the location of the selected slice of the reference dataset. In other words, the process may link the location information (e.g., the position and/or orientation of the TRUS probe) corresponding with the current image with the corresponding location of the selected image slice (or at least one image slice) of the reference dataset. Once the location information is linked, images acquired in real time (e.g., current image) at a certain position and/or orientation (of the TRUS probe) may be linked to images in the reference dataset with the same (or similar) position and/or orientation. The process may update the linked location continuously in real time, if desired.

In accordance with some embodiments, the process may link the location of the current image with the location of the selected slice of the reference dataset using any suitable method or methods. For example, the process may perform an initial linking as described above. Thereafter, the process may use image recognition methods to recognize features of the prostate in the current image and select a corresponding image (e.g., a selected image) in the reference dataset. The location of this selected image may then be linked to the location of the current image. This may account for deformation that may occur when catheters are inserted within the prostate. For example, when inserting an object such as a catheter within the prostate, the catheter may dislocate the prostate at least a few centimeters superiorly and/or change the shape of the prostate. For example, the catheter may elongate the prostate and as such the slices coordinates may not have a one-to-one correspondence. Accordingly, embodiments of the present system may employ image-based methods (e.g., which may employ image registration methods, if desired) to continuously link the location of the current image with a reference image selected from the reference dataset, if desired.

After completing act 413, the process may continue to act 415.

During act 415, the process may obtain a CBS which corresponds to the selected image from the reference dataset. Accordingly, the process may obtain the CBS from the reference dataset that is a CBS of the selected image slice. This CBS may be referred to as a selected CBS. As the selected image slice may be considered a closest fit to the current image, the CBS may also be considered a closest fit (e.g., a closest matching) CBS to the current image.

In accordance with some embodiments, the process may perform an image registration process to register the selected image slice from the reference dataset onto the current image (e.g., a live image). This image registration process may be performed using any suitable image registration method such as an automated registration algorithm to register images as may be disclosed in Applicant's prior co-pending application No. PCT/IB2013/059989, entitled "Assisting Apparatus for Assisting in Performing a Brachytherapy," filed on Nov. 8, 2013, and published as WO 2014/091330 A1 on Jun. 19, 2014, the contents of each of which are incorporated herein by reference.

After completing act 415, the process may continue to act 416 where the process may determine position and/or orientation for the grid template. In accordance with some embodiments, the position and/or orientation of the grid template may be set by the system and/or user. For example, in accordance with some embodiments, the position and/or orientation of the grid template may be set by the user. In accordance with yet other embodiments, the system may determine a position and/or orientation of the grid template and may render this information for the convenience of the user who may then set the position and/or orientation of the grid template accordingly. In yet other embodiments, the system may control actuators to set the position and/or orientation of the grid template as may be discussed elsewhere.

In accordance with some embodiments, the process may determine the position and/or orientation of the grid template in accordance with one or more of the location constraints. For example, in accordance with some embodiments the process may determine the position and/or orientation of the grip template in accordance with one or more of the location constraints so that that one or more of the catheters may intersect their PCIP and/or do not intersect the RAs, as may be desired by a user. The position and/or orientation of the grid template may be determined using any suitable method.

In accordance with some embodiments, the process may determine the position and/or orientation (hereinafter location) of the grid template at least based upon one or more of the location constraints (e.g., the PCIPs, and/or the RAs), position and/or orientation of the TRUS probe, the current image, and/or the reference dataset using any suitable method such as geometrical methods operating in accordance with embodiments of the present system. For example, as the TRUS probe has been previously linked (e.g., during act 413), its location relative to one or more of the current image and the reference dataset may be determined. The process may then use one or more location constraints such as the PCIPs and/or RAs to determine location and/or orientation of the grid template so that projected trajectories of one or more of the catheters which extend through and/or from the grid template intersect at their corresponding PCIPs while not entering the RAs. The process may further determine a location (e.g., in an array of the grid template) for one or more of the catheters, if desired. The process may perform these determinations in real time and/or when certain conditions are determined to occur such as in response to a user request, insertion of a catheter, etc.). For example, the process may determine a position and/or orientation for the grid template at least once.

In accordance with some embodiments, the grip template may include an array of grid template portions (e.g., quadrants, etc.) which may be adjustable in position and/or orientation relative to each other. For example, in accordance with some embodiments the grid template may include four quadrants one or more of which may be articulable relative to the other. For example, after insertion of a catheter, the process may determine a desired position and/or orientation of the grid template or portions thereof for insertion of another catheter. Accordingly, one or more catheters may be inserted using the same or different grid template positions and/or orientation as may be used for one or more other catheters. A catheter steering system may include actuators to control the position and/or orientation of one or more portions of the grid template.

In accordance with some embodiments, the process may determine a planned trajectory for one or more of the catheters which may represent a vector between a point on the catheter such as its tip (e.g., the distal end) and the PCIP of the catheter. Accordingly, it may be assumed that if the catheter extends along its planned trajectory, it may be expected to intersect or substantially reach its PCIP absent any deviation from the trajectory. Thus, if the catheter is extended along its longitudinal axis (e.g., $z_c$ as shown in FIG. 2A by a user and/or by a steering mechanism of the catheter) it may be expected to intersect or substantially intersect its PCIP absent any deviation from the estimated trajectory. After a planned trajectory is determined for a catheter, the process may inform a user of such determination (e.g., so that a user may steer the catheter to follow the estimated trajectory) and/or steer the catheter in accordance with the estimated trajectory.

In accordance with some embodiments, the planned trajectory of a catheter may further be determined in accordance with one or more of a current position and/or orientation of the TRUS probe, the selected CBS, one or more of the location constraints, the current image, and/or the reference dataset. For example, the trajectory may be determined in accordance with the location constraints so that it does not intersect any RAs, does not exit the prostate, etc. The grid template may then be located (e.g., positioned by a user and/or the system) in accordance with the estimated position and/or orientation of the catheter or vice versa.

In accordance with some embodiments, if one or more PCIPs are not defined (e.g., by the user and/or system), the process may skip the act of determining the planned trajectory of one or more of the catheters. This may be useful when manual catheter manipulation is desired by the user, etc. In this case, the process may inform a user of desired position and/or orientation of the grid template and/or may determine an actual position and/or orientation of the grid template for later calculations, if desired.

In accordance with some embodiments, after a grid template position and/or orientation is determined (e.g., so as to set one or more of the catheters to their planned trajectories), the process may inform a user of this position and/or orientation using any suitable method such as by rendering such information on display of the system, or may control actuators of the system to set the position and/or orientation of the grid template to the desired position and/or orientation, if desired. For example, FIG. 6, shows a window 666 illustrating catheter parameters which may be rendered where when a user selects a PCIP 664 (e.g., by right clicking on the PCIP). The window 666 may include information about the PCIP 664 and corresponding catheter such as type, current parameters (e.g., not yet inserted, automatically steered, model, manufacture, current settings, etc.), distance from tip to PCIP (e.g., $z_c$), location in grid array (col., row, etc.), etc., as may be set by the system and/or user.

Referring back to the linking, once the location information is linked, images acquired in real time (e.g., current image) at a certain position and/or orientation (of the TRUS probe) may be easily linked to images in the reference dataset with the same (or similar) position and/or orientation the current image, and the reference dataset. Thus, a location of the TRUS probe may be linked to a corresponding image slice (or slices) in the reference dataset. This may conserve system resources during a procedure and may save time. After completing act 416, the process may continue to act 417.

During act 417, the process may determine whether catheter insertion process has started. Accordingly, if it is determined that the catheter insertion process has started, the process may continue to act 418. However, if it is determined that catheter insertion process has not started, the process may repeat act 417. The process may determine that the catheter insertion process has started using any suitable method. For example, in accordance with some embodiments, a user and/or the process may request to begin the catheter insertion process. In yet other embodiments, the catheter insertion process may be determined to start when a location (e.g. position and/or orientation, etc.) of a catheter (as determined by its tip) has been determined to change beyond a threshold value.

During act 418, the process may optionally track one or more of the catheters to determine an estimated trajectory of one or more of the corresponding catheters. When tracking the catheters, the process may determine information related to one or more of location, orientation, actual trajectory, travel path (e.g., as may be determined by tracking location over time, etc.), and extension (e.g., in the z-direction) of one or more corresponding catheters in real time. This information may then be stored as catheter location information in a memory of the system for later use and/or may be used to determine the estimated trajectory of one or more of the corresponding catheters. For the sake of clarity and without limitation, it will be assumed that each catheter may include a single tracking element located at its distal end and that the process may track the location (e.g., position and/or orientation) of a corresponding catheter by tracking this tracking element. In accordance with some embodiments, the estimated trajectory of a catheter may be determined based upon the determined position and/or orientation of the distal end of the catheter such. Accordingly, the location of a catheter may refer to a location at its distal end. Thus, the process may track the tracking element of a catheter over time as the catheter travels and form corresponding location information. The process may then further determine the catheter's actual travel path, orientation, trajectory, and/or extension in the z-axis (hereinafter z extension) based at least in part upon the location information generated by the tracking.

In accordance with some embodiments, knowledge of the grid entry point of the catheter (e.g., X-Y coordinates of the grid location which may correspond with a column and/or row of the grid; where a surface of the grid corresponds to z=0) and of the history of the catheter trajectory may be used by the process to calculate estimated catheter trajectory. Sensors, such as the EM sensors, may provide position and/or orientation of the catheter.

Further, in accordance with some embodiments, the process may determine whether a catheter may be set as a current catheter using any suitable method. For example, in accordance with some embodiments, if it is determined that the catheter is being manipulated, the process may set this catheter as a current catheter. Accordingly, when a user moves a catheter (e.g., in a z-direction of the catheter), the process may sense this movement and determine that this catheter of the plurality of catheters is a current catheter. However, in accordance with yet other embodiments, the process may determine a current catheter as a catheter whose movement is requested by the process. For example, movement of the catheters may be selected in a certain order and/or pattern (e.g., relative to an array of the grid template) as may be set by the system and/or user (e.g., in accordance with user settings). Accordingly, the process may determine a current catheter. In accordance with yet other embodiments, a current catheter may be determined at least based upon user and/or system settings. In accordance with yet other embodiments, a user may select a catheter to be a current catheter. After completing act 418, the process may continue to act 419.

During act 419, the process may apply elastic (deformable) registration constraints during the catheter insertion process in which at least one catheter (e.g., a current catheter) may be inserted into the prostate. These constraints may, without limitation, take into account several variables such as: a) push of the prostate towards the base; b) swelling of the prostate in the anterior-posterior and lateral directions; and/or c) apriori prostate shape constraints, in the event that the quality of the live image is degraded by the presence of the catheters. The deformation vectors may be the result of the elastic image registration, which in turn may be computed with or without the elastic (deformable) registration constraints. Depending on the dimensionality of the live image (2D or 3D) and the type of registration chosen, the deformation vectors may be 2D (inside the current image plane for 2D live image, registered to the corresponding planar cross-section of the prior 3D image; "corresponding" meaning: based on the spatially tracked position of the 2D live image plane), or 3D (in case the live image is 3D also, or in case a "2D to 3D" registration is carried out, i.e., registering the live 2D image to the 3D prior image and allowing out-of-plane translation/rotation/shearing/deformation). The constraints could be applied during the registration, e.g., by defining an image-similarity metric in which such potential registrations are penalized that "violate" any of the constraints.

As catheters and/or other objects are inserted into the prostate, the prostate may change its shape. Accordingly, the process may form or otherwise update deformation vectors in accordance with registration constraints so as to take into account the deformation of the prostate. If desired, the process may obtain information related to location and/or orientation of one or more catheters and/or portions thereof (e.g., distal ends) from sensors of the system such as may be location information. After completing act 419, the process may continue to act 421.

During act 421, the process may modify the selected CBS in accordance with the deformation vectors so as to update the selected CBS. Accordingly, the process may apply the deformation vectors to the CBS (e.g., see, 545, FIG. 5) so as to modify the selected CBS (which may be referred to as a modification contour) so as to represent most current estimated boundaries of the prostate (e.g., a most current CBS).

With reference to FIG. 5, although the selected CBS (e.g., 545) and the modification contour (e.g., 547) are illustrated as closed surfaces in the present embodiments, in yet other embodiments, it is envisioned that the CBS and/or modification contour may include open curves and/or discontinuous curves, if desired.

As discussed above, as needles are inserted into the prostate, the prostate may change its shape (e.g., deform) and the process may update deformation vectors to take this change of shape into account. The process may calculate registration constraints which take into account the deformation of the prostate and update the deformation vectors according to the registration constraints. Then, the process may update the selected CBS in accordance with these updated deformation vectors so as to form a current CBS which may act as a modification contour which, as discussed above, may estimate the deformed boundaries of the prostate. After completing act 421, the process may continue to act 423.

During act 423, the process may determine whether there is a significant change in the estimated boundaries of the prostate due to insertion one or more of the catheters into the prostate. Accordingly, if it is determined that there is a significant change in the estimated boundaries of the prostate, the process may continue to act 425. However, if it is determined that there is no significant change in the estimated boundaries of the prostate, the process may continue to act 426. The process may determine that there is a significant change in the estimated boundaries of the prostate using any suitable method such as by comparing corresponding points of the updated selected CBS (which may be a most recent CBS) with the selected CBS before the (corresponding) modification and calculating an absolute value (CAV) of a difference between these points. Accordingly, if it is determined that the CAV is greater than a threshold distance value, the process may determine that there is a significant change in the estimated boundaries of the prostate. However, if the absolute value of this calculated absolute value is less than or equal to the threshold value, the process may determine that there is no significant change in the estimated boundaries of the prostate.

However, in yet other embodiments, the process may use any other suitable method such as image analysis methods or the like to determine whether there has been a significant change in the estimated boundaries of the prostate.

In accordance with embodiments of the present system, the process may skip act 423 and continue to act 426. For example, if it is determined that there are no predefined PCIPs defined (e.g., during act 406), the process may continue from act 421 to 426. Similarly, if the system (e.g., based upon system settings) and/or user selects to skip act 423, the process may continue from act 421 to act 426. A user may objectively determine to skip act 423 when conditions may warrant so such as when broader constraints, such as a need to remain inside the prostate and/or close to boundaries of the prostate may warrant such on an individual basis.

During act 425, the process may re-optimize the PCIPs so as to update planned placement of remaining catheters. As used herein, the remaining catheters may refer to catheters which have not yet been inserted into the prostate or have not yet been fully inserted into position within prostate. Accordingly, the process may perform a dynamic catheter re-planning process to re-optimize the PCIPs of these remaining catheters in accordance with the determined current prostate contours (e.g., in 2D or 3D). Accordingly, the process may determine which catheters have not yet been inserted into the prostate and re-optimize placement of these catheters. Methods used to perform the re-optimization may be the same as, or similar to, those used for performing the determination of optimized PCIPs act 406 however, the re-optimization may use the most current estimated boundaries of the prostate (e.g., as may be represented by the most current modified CBS) to determine the re-optimized PCIPs as opposed to the original boundaries (as may be represented by the corresponding original CBS) of the prostate used during act 406. Accordingly, during act 425, PCIPs may be determined so that distal ends of one or more of the catheters are expected to be situated in the boundary region of the prostate (e.g., as defined by the most current CBS which define the most current estimated peripheral boundaries of the prostate) when at their corresponding PCIPs.

This re-optimization act 425 may be performed when it is determined that there is a significant change in the estimated prostate boundaries due to insertion of the initial catheters. Further, the planned placement for the remaining catheters may then be re-optimized by the process using the most current prostate contours. After completing act 425, the process may continue to act 426.

With regard to the estimated trajectory, this trajectory is where the catheter is expected to end up given its current position and orientation and may be obtained by the process solely from information related to the position/orientation of the sensor at the distal end of the catheter. The planned trajectory is where the process may determine that the catheter should go and may be obtained based upon information related to a combination of information such as a grid entry hole for the corresponding catheter, a PCIP for the corresponding catheter, the RA, etc.

During act 426, the process may optionally update the planned trajectories of one or more of the remaining catheters. This may correct for changes (e.g., updates) of the CBS and/or PCIPs. The process may update the planned trajectories for the remaining catheters using any suitable method such as those described during act 416. However, the process may use the updated PCIPs, estimated trajectories, and updated actual locations of corresponding catheters when available. For example, the process may track one or more of the remaining catheters to determine an actual location of its tip. Then, the process may update a catheter's planned trajectory at least based upon the catheter's actual location and/or estimated trajectory in accordance with the catheter's most recent (e.g., updated or original) PCIP.

The process may then render information related to the estimated and/or planned trajectories of the one or more remaining catheters for the convenience of a user (as discussed during act 416) and/or may control a steering mechanism of one or more of the remaining catheters accordingly so as to guide a selected catheter to its PCIP in accordance with, for example, the planned PCIP for the catheter. In accordance with some embodiments, the controller may control the steering mechanism to advance or retract the catheter only a threshold distance (as may be set by the user and/or system) such as up to 5 mm over any given period of time (e.g., 30 seconds). However, other values or ranges of values for these values are also envisioned.

In accordance with some embodiments, the process may automatically detect bending or deflection of a catheter. The process may determine proper actions for correction (e.g., steering, withdrawal, insertion, etc.) and may render such information to guide the user so that so that the trajectory of the catheter may be corrected and may be within a certain threshold value that may be acceptable. For example, the process may determine whether a catheter is bending or deflecting beyond a threshold value and, in the affirmative, may take appropriate actions to correct for the deflection either automatically or by rendering information for a user to make the correction manually. In accordance with some embodiments, catheter bending or deflection may be identified by a detecting a change in an orientation (e.g., angular orientation) of a tip of a catheter (as may be measured by a catheter angle) that is greater than a corresponding threshold angular value (e.g., t_alpha as may be defined by the system and/or user), or a change in an x-y position (i.e., within the transverse plane) of a tip of a catheter that is greater than a corresponding threshold value (e.g., t_deltaXY as may be defined by the system and/or user). More particularly, if the catheter angle relative to the z-axis (e.g., relative to the x and y planes) is determined to be greater than t_alpha, the process may render information to inform a user that the catheter angle is greater than a permissible value. Similarly, if an x-y catheter tip position change is determined to be greater than t_deltaXY for a given unit of translation along the z axis (e.g., 1 mm), the process may render information to inform a user of such determination and may record a position of the tip of the catheter. The process may then inform the user to pull the corresponding catheter back to a smaller z position, in order to eliminate and avoid the catheter bending/deflection or may take action to automatically by controlling a controller at least based upon a the recorded catheter tip position.

In accordance with some embodiments, the process may track catheters, update PCIPs, and/or update estimated trajectories for catheters in real time. After completing act 426, the process may continue to act 427.

During act 427, the process may form one or more composite images such as a current segmented live 2D TRUS image which may, for example, include the most current modified selected CBS (i.e., the modification contour) superimposed upon the current image to form a composite image. For example, with reference to FIG. 5, the process may obtain the current image such as the image 548 and superimpose the modification contour 547 upon the current image to form a current segmented live 2D TRUS image 550.

In accordance with some embodiments, the process may further superpose or superimpose information related to one or more of the PCIPs, estimated and/or actual trajectories, and/or parameters (e.g., catheter range, catheter settings, catheter trajectory, estimated and/or planned trajectories, etc.) of at least one of the catheters upon the current image (e.g., the live 2D TRUS image) or another representation of the current image (e.g., a copy of the current image so as to form another composite image), as may be desired by the system and/or user.

For example, the process may determine catheter range which may indicate a difference in a distance between a catheter (e.g., as measured at its tip) and the current image plane (or PCIP if desired and which may be represented as rangePICP). The process may then form an alpha, numerical, and/or graphical representation of the catheter range and render this information for a user. With regard to determining the catheter range, the process may compare an actual location of a catheter (as may be measured at the tip of the catheter) with a current image plane. In other words, the process may determine a distance from the tip (e.g., the tip at the distal end) of one of the catheters to a current image plane, an estimated intersection of the catheter with a current image plane, and/or an actual intersection of the catheter with the current image plane, as may be selected by the system and/or user. For example, FIG. 8A shows a screen shot 800A of an estimated intersection of a catheter whose tip has not yet reached the current image plane superposed upon a current image in accordance with embodiments of the present system; FIG. 8B shows a screen shot 800B of an actual intersection point for a catheter whose tip has reached the current image plane superposed upon a current image in accordance with embodiments of the present system; and FIG. 8C shows a screen shot 800C of an actual intersection point for a catheter whose tip has passed the current image plane superposed upon a current image in accordance with embodiments of the present system.

With reference to FIG. 8A, if it is determined that the tip of the catheter has not yet intersected a current image plane, the process may determine and thereafter indicate an estimated intersection of the catheter with the current image plane (e.g., an image plane currently being viewed) using any suitable representation such as a dot 864R or other desired shape (e.g., "○," "×," "+," etc.), as may be desired. The dot 864R may be highlighted using any suitable highlighting such as a red highlighting to indicate that the catheter has not yet intersected the current image plane. The process may determine the estimated intersection of the catheter with the current image plane at least based upon an estimated trajectory of the catheter and a location of the current image plane. The process may further render a circle which may indicate a desired point or area through which the tip of the catheter should pass through.

With reference to FIG. 8B, if it is determined that the tip of the catheter has intersected and is at (e.g., within a threshold distance from) the current image plane, the process may indicate the point of intersection (e.g., as determined by tracking an actual location of the catheter) using any suitable representation such as a dot 864G which may be similar to the dot 864R. However, the dot 864G may be highlighted using any suitable highlighting such as a green highlighting to emphasize that the catheter has intersected and is at the current image plane. In accordance with some embodiments, a location of the point of intersection of one or more of the catheters (e.g., a selected catheter such as the current catheter) may be represented using audible methods which may be rendered on a speaker of the system. For example, the process may render a pitch variably in accordance with a distance (e.g., an absolute value of the distance) between the catheter tip and a desired location/intersection point or may indicate the distance using words which may represent a distance in one or more axes (e.g., 5 mm, 4 mm, 1 mm, −1 mm, −3 mm, etc. to the right, to the left, +4 mm z axis, −4 mm z axis, etc.). Thus, as a catheter tip approaches a desired location (e.g., a predefined intersection point), the process may decrease the pitch and vice versa and render this information for the convenience of a user. Accordingly, when the tip of the catheter intersects the desired intersection point, the pitch may be substantially represented using a default frequency (e.g., 0 Hz as may be set by the system and/or user). Conversely, as the tip of the catheter moves away from a desired intersection point, the pitch may increase. In accordance with yet other embodiments, distance information may be rendered using audible methods such as may be provided using text-to-speech TTS methods. In accordance with some embodiments, an absolute value of the he difference between the catheter tip and a desired location/intersection point may be represented as error information. Then, the process may render information related to the error information. For example, if the error is increasing, the process may increase the pitch. Accordingly, a large error will result in a high pitch. Conversely, as the error decreases, the pitch may decrease. Accordingly, a small error will result in a low pitch. Thus, as the pitch substantially decreases and approaches 0 (or some default value as may be set by the system and/or user), the user may determine that the catheter tip has reached its desired location. However, if the pitch increases, the use may determine that the catheter tip is traveling away from the desired location.

With reference to FIG. 8C, if it is determined that the tip of the catheter has intersected and extended beyond the current image plane (e.g., by a threshold distance), the process may indicate the point of intersection (e.g., as determined using previous tracking information obtained when the tip of the catheter intersected the current image plane) using any suitable representation such as a dot 864Y which may be similar to the dots 864R and 864G. However, the dot 864Y may be highlighted using any suitable highlighting such as a yellow highlighting to emphasize that the catheter has intersected and has extended past the current image plane. In accordance with some embodiments, a hyperechoic spot may be visible in a current image and provide additional qualitative validation. For example, when the catheter tip extends past the current image plane, the current image plane may include a cross-section of the body of the catheter. This may be visible as a hyperechoic (bright) region in the current image and may confirm a location where the corresponding catheter intersected the current image plane. However, due to catheter bending, the tip of the catheter may or may not have intersected the current image plane at this point due to catheter bending.

In accordance with yet other embodiments, the process may provide an indication of a distance between a tip of a catheter and a selected object such as a selected point, an RA, and/or a selected image slice such as the currently-viewed image slice. This indication of distance may be provided using any suitable rendering method such as visual, audible, and or haptic methods. For example, in accordance with some embodiments, the process may form audio pitch and tones which may decrease as the tip of the catheter approaches the currently-viewed image slice and vice versa. Accordingly, the audio pitch and tone may be equal to, or substantially equal to, zero when the tip of the catheter is determined to be at the currently-viewed image slice (or other selected point), and each or one of the audio pitch and tone may increase as the tip of the catheter is moved away from the currently-viewed image slice. Similarly, haptic feedback may be provided to a user via a vibrator coupled to the catheter and which may decrease vibration frequency and/or amplitude when the tip of the catheter approaches the currently-viewed image slice. Conversely, the vibration frequency and/or amplitude may increase when the tip of the catheter moves away from the currently-viewed image slice. In yet other embodiments, a distance between the catheter tip and the currently viewed image slice may be provided using numerals 866Y such as shown in FIG. 8C. By providing audio, visual, and/or haptic feedback to indicate a distance between a tip of a catheter and an image plane, a clinician may more readily navigate the catheter tip to a desired location.

In accordance with some embodiments, the process may render a current image and one or more reference images such as an image slice corresponding with a location of the current image selected from the reference dataset.

After completing act 427, the process may continue to act 429 where the process may render one or more of the composite images formed during or after the re-optimization act 425 such as the current segmented live 2D TRUS image on a display of the system for the convenience of the user. The process may further provide an interactive user interface (UI) with which a user may interact with the process to, for example, select portions of the rendered images such as the current segmented live 2D TRUS image and/or composite image for performing certain actions, such as changing magnification, selecting features, etc. The process may further provide a user interface so that a user may select other images for rendering such as the current image, one or more image slices of the reference dataset, image slices (e.g., image planes), etc. The process may further render information related to an actual location, estimated trajectories, estimated distances, planned trajectories, etc. for one or more of the catheters as may be selected by the system and/or user (e.g., one or more remaining catheters, if desired). For example, in accordance with some embodiments, the process may provide a user interface which may allow a user to view and/or rotate the current segmented live 2D TRUS image so as to view the current segmented live 2D TRUS image in 3D and/or actual and projected trajectories of one or more of the catheters. After completing act 429, the process may continue to act 431.

During act 431, the process may store information obtained and/or generated by the process in a memory of the system for further use. After completing act 431, the process may continue to act 433.

During act 433, the process may update the current image with a live image obtained from the TRUS probe. This act may be similar to act 409. In accordance with some embodiments, this updating may act may occur when certain conditions are met, such as when a user inserts a catheter or a group of catheters (e.g., places a catheter in a desired position as may be indicated by the process), when a certain time elapses (e.g., an update time such as 1/15th of a second, etc.), when a user requests an update, etc. After completing act 433, the process may repeat act 418.

Thus, embodiments of the present system may register a pre-acquired planning image such as an image from the reference dataset onto a live image such as the current image. Peripheral boundaries of an organ determined for the reference dataset may then be modified in accordance with determined changes in boundaries of the organ and superposed upon the current image so as to provide enhanced catheter guidance which may increase the accuracy of catheter location.

It is further envisioned that embodiments of the present system may provide a process to track, assess, and/or determine an estimated trajectory of one or more catheters. For example, in accordance with some embodiments, the process may determine a current location of a catheter tip using spatial tracking information generated by one or more sensors of the system. The process may then determine an estimated catheter trajectory which may be represented as a ray (e.g., a vector) which may start at a determined current location of the catheter tip and extend in a direction which is in accord with a current orientation of the tip of the catheter. The process may further detect and store information related to the determined estimated catheter trajectory (e.g., as may be represented using a ray), and/or catheter position and/or orientation. The process may do this in real time. The process may then determine and/or refine one or more of estimated and/or planned catheter trajectories, estimated intersection with one or more image planes, distance (e.g., actual and/or estimated) to a point of intersection with an image plane, catheter bending and/or catheter deflection at least based upon the information related to the catheter position and/or orientation that may be stored in a memory of the system. For example, if the catheter is bending, the direction and/or amplitude of the ray representing its previous estimated trajectory may change along a path of travel of the tip of the catheter. However, in yet other embodiments, the process may determine that a catheter is bending when a change in the path of travel of the tip of the catheter is determined to be greater than a threshold value (e.g., the path may form an arc).

Embodiments of the present system may provide a user interface (UI) such as a graphical user interface (GUI) which may render a visualization of current as well as predicted catheter positions (e.g., as may be measured at the tracked tip of the catheter). The visualization may further include a representation of intersection points such as actual intersection points and/or estimated intersection points, planned trajectory, estimated trajectory, which may be superposed upon current live ultrasound imaging plane(s), arbitrary image planes, and/or pre-acquired reference image frames. In accordance with embodiments of the present system, spatial tracking of an ultrasound probe may be used to determine a position of a live ultrasound image in tracking space, the latter of which may be used to determine an intersection of predicted and/or actual catheter trajectory with live and/or reference images.

Further, in accordance with some embodiments, in live transverse image planes, an intersection with the catheter trajectory (e.g., estimated) can be visualized by rendering a marker whose characteristics such as color, shape, size, intensity may be selected to indicate whether a tip of a corresponding catheter is in front of, at, or behind a current image plane (as shown in FIG. 8x).

In accordance with yet other embodiments, the system may render a visualization of a trajectory of a catheter relative to, for example, a live image and/or an image slice selected from a reference dataset. Accordingly, the system may provide an interface (e.g., a GUI) with which a user may select image slices from the reference dataset.

Figure 9:
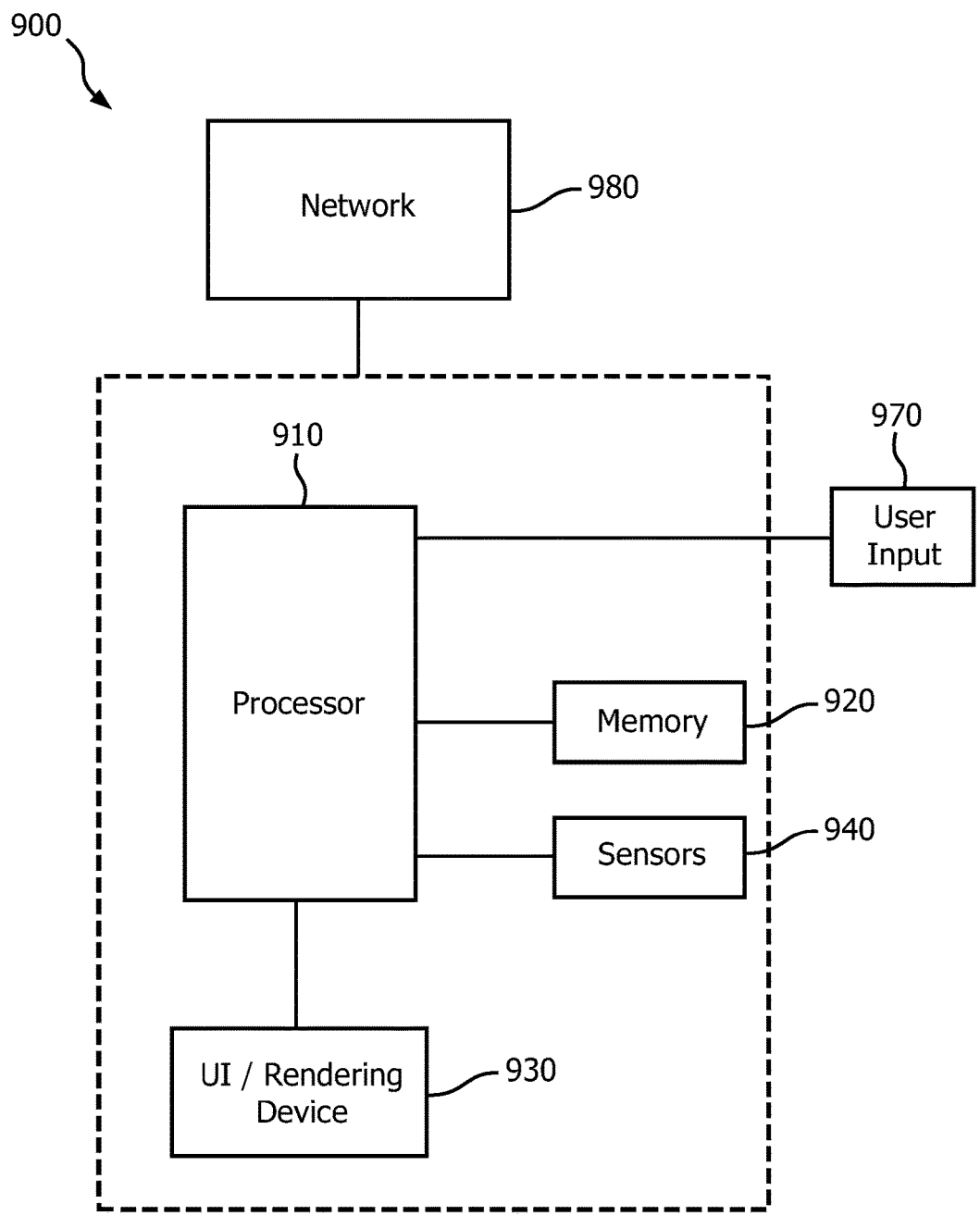
FIG. 9 shows a portion of a system in accordance with embodiments of the present system.

FIG. 9 shows a portion of a system 900 in accordance with embodiments of the present system. For example, a portion of the present system may include a processor 910 (e.g., a controller) operationally coupled to a memory 920, a user interface (UI) and/or rendering device such as a display 930 for rendering the UI and further images, e.g., a touch sensitive display, sensors 940, a network 980, and a user input device 970. The memory 920 may be any type of device for storing application data as well as other data related to the described operation. The application data and other data are received by the processor 910 for configuring (e.g., programming) the processor 910 to perform operation acts in accordance with the present system. The processor 910 so configured becomes a special purpose machine particularly suited for performing in accordance with embodiments of the present system.

The user input 970 may include a keyboard, a mouse, a trackball, or other device, such as a touch-sensitive display, which may be stand alone or be a part of a system, such as part of a personal computer, a personal digital assistant (PDA), a mobile phone (e.g., a smart phone), a monitor, a wearable display (e.g., smart glasses, etc.), a smart- or dumb-terminal or other device for communicating with the processor 910 via any operable link. The user input device 970 may be operable for interacting with the processor 910 including enabling interaction within a user interface (UI) as described herein. Clearly the processor 910, the memory 920, display 930, and/or user input device 970 may all or partly be a portion of a computer system or other device such as a client and/or server.

The methods of the present system are particularly suited to be carried out by a computer software program, such program containing modules corresponding to one or more of the individual steps or acts described and/or envisioned by the present system. Such program may of course be embodied in a non-transitory computer-readable medium, such as an integrated chip, a peripheral device or memory, such as the memory 920 or other memory coupled to the processor 910.

The program and/or program portions contained in the memory 920 may configure the processor 910 to implement the methods, operational acts, and functions disclosed herein. The memories may be distributed, for example between the clients and/or servers, or local, and the processor 910, where additional processors may be provided, may also be distributed or may be singular. The memories may be implemented as electrical, magnetic or optical memory, or any combination of these or other types of storage devices. Moreover, the term "memory" should be construed broadly enough to encompass any information able to be read from or written to an address in an addressable space accessible by the processor 910. With this definition, information accessible through a network such as the network 980 is still within the memory, for instance, because the processor 910 may retrieve the information from the network 980 for operation in accordance with the present system.

The processor 910 is operable for providing control signals and/or performing operations in response to input signals from the user input device 970 as well as in response to other devices of a network and executing instructions stored in the memory 920. The processor 910 may include one or more of a microprocessor, an application-specific or general-use integrated circuit(s), a logic device, etc. Further, the processor 910 may be a dedicated processor for performing in accordance with the present system or may be a general-purpose processor wherein only one of many functions operates for performing in accordance with the present system. The processor 910 may operate utilizing a program portion, multiple program segments, or may be a hardware device utilizing a dedicated or multi-purpose integrated circuit. Embodiments of the present system may provide fast imaging methods to acquire images and generate corresponding image information.

Embodiments of the present system may provide clinicians with quantitative knowledge of organ boundaries (e.g., of the prostate) during tool insertion in interventional therapy procedures (e.g., high-dose-rate (HDR) brachytherapy, cryotherapy, hyperthermia catheter insertion and the like). Accordingly, embodiments of the present system may be operative to decrease uncertainty associated with determining the organ boundaries and provide robust real-time image guidance during tool-insertion procedures. This may enhance accuracy of tool insertion. Embodiments of the present system may also reduce or eliminate the need for repeat tool insertion which may shorten clinical procedure time.

Embodiments of the present system may provide a system and method which may provide a user interface (UI) with which a user may interact and which may render segmented images of an organ such as a prostate during catheter implantation in real time. Accordingly, embodiments, of the present system may generate and render a user interface (UI) which may include a visualization of a desired organ such as the prostate and its boundaries by slice to provide real-time guidance to a user such as a clinician during an interventional procedure in which one or more catheters may be inserted into the desired organ. This may reduce time required to perform the interventional procedure and may increase accuracy of the procedure. Embodiments of the present system may provide real-time segmentation for internal radiation therapy procedures such as brachytherapy and the like in which live image slices of an organ and/or the boundaries of the organ in each corresponding slice may be determined and rendered.

Further, embodiments of the present system may provide a quantitative guide during catheter insertion and may ease the process of guiding catheters to desired locations. Accordingly, embodiments of the present system may result in more accurate adherence to clinical objectives and may shorten clinical procedure times. While embodiments of the present system were described with respect to HDR brachytherapy procedures, it is envisioned that other embodiments of the present system may include other clinical target applications such as low-dose rate (LDR) brachytherapy procedures, transperineal prostate therapy, prostate biopsy, and/or non-prostate applications.

While the present invention has been shown and described with reference to particular exemplary embodiments, it will be understood by those skilled in the art that present invention is not limited thereto, but that various changes in form and details, including the combination of various features and embodiments, may be made therein without departing from the spirit and scope of the invention.

Further variations of the present system would readily occur to a person of ordinary skill in the art and are encompassed by the following claims.

Finally, the above-discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art without departing from the broader and intended spirit and scope of the present system as set forth in the claims that follow. In addition, the section headings included herein are intended to facilitate a review but are not intended to limit the scope of the present system. Accordingly, the specification and drawings are to be regarded in an illustrative manner and are not intended to limit the scope of the appended claims.

The section headings included herein are intended to facilitate a review but are not intended to limit the scope of the present system. Accordingly, the specification and drawings are to be regarded in an illustrative manner and are not intended to limit the scope of the appended claims.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function;

e) any of the disclosed elements may be comprised of hardware portions (e.g., including discrete and integrated electronic circuitry), software portions (e.g., computer programming), and any combination thereof;

f) hardware portions may be comprised of one or both of analog and digital portions;

g) any of the disclosed devices or portions thereof may be combined together or separated into further portions unless specifically stated otherwise;

h) no specific sequence of acts or steps is intended to be required unless specifically indicated;

i) the term "plurality of" an element includes two or more of the claimed element, and does not imply any particular range of number of elements; that is, a plurality of elements may be as few as two elements, and may include an immeasurable number of elements; and j) the term and/or and formatives thereof should be understood to mean that only one or more of the listed elements may need to be suitably present in the system in accordance with the claims recitation and in accordance with one or more embodiments of the present system.

What is claimed is:

1. An interventional therapy system, comprising:
at least one controller:
configured to obtain a reference image dataset of an object of interest (OOI);
configured to segment the reference image dataset to determine peripheral outlines of the OOI in a plurality of image slices;
configured to acquire a current image of the OOI using an ultrasound probe;
configured to select a peripheral outline of a selected image slice of the plurality of slices of the reference image dataset which is determined to correspond to the current image;
configured to deformably register the selected image slice of the plurality of slices of the reference image dataset with the current image to obtain at least one deformation vector; and
configured to apply the at least one deformation vector to the selected peripheral outline of the selected image slice selected from the reference image and corresponding to the current image to obtain a modified peripheral outline of the OOI in the selected image slice of the reference image dataset that represents a most current estimated peripheral outline by modifying the selected peripheral outline of the selected image slice of the plurality of slices of the reference image dataset in accordance with the at least one deformation vector without using any peripheral outline in the current image.

2. The interventional therapy system of claim 1, further comprising a rendering device, wherein the controller is further configured to render the current image with the modified selected peripheral outline of the selected image slice of the plurality of slices of the reference image dataset superposed thereon using the rendering device.

3. The interventional therapy system of claim 1, further comprising at least one sensor which provides location information comprising at least one of a position and an orientation of the ultrasound probe when the current image was acquired.

4. The interventional therapy system of claim 3, wherein the controller is configured to select the selected image slice of the plurality of slices of the reference image dataset in accordance with the location information of the current image.

5. The interventional therapy system of claim 1, wherein the deformation vector is formed in accordance with elastic deformation constraints.

6. The interventional therapy system of claim 1, wherein the current image comprises an image slice having a slice type selected from one of an axial or sagittal slice types and the image slices comprise a plurality of images of the same slice type as the current image.

7. The interventional therapy system of claim 1, wherein the controller is further configured to determine whether the modified selected peripheral outline of the image slice of the plurality of slices of the reference image dataset exceeds a threshold boundary change.

8. The interventional therapy system of claim 7, wherein the controller is further configured to optimize placement of catheters when it is determined that the modified selected peripheral outline of the image slice of the plurality of slices of the reference image dataset exceeds the threshold boundary change.

9. The interventional therapy system of claim 1, wherein the controller is further configured to select an image slice from the plurality of slices of the reference dataset which is determined to correspond to the current image.

10. An interventional therapy system, comprising:
at least one controller:
configured to obtain a reference image dataset of an object of interest (OOI);
configured to segment the reference image dataset to determine peripheral outlines of the OOI;
configured to acquire a current image of the OOI using an ultrasound probe;
configured to select a cross-section of the reference image dataset which is determined to correspond with the current image;
configured to select a peripheral outline of the segmented reference image dataset that correspond with the selected cross-section of the reference image dataset;
configured to deformably register the selected cross-section of slices of the reference image dataset with the current image to obtain at least one deformation vector; and
configured to apply the at least one deformation vector to the selected peripheral outline of the selected image slice selected from the reference image and corresponding to the current image to obtain a modified peripheral outline of the OOI in the selected image slice of the reference image dataset that represents a most current estimated peripheral outline by modifying the selected peripheral outline in accordance with at least one deformation vector without using any peripheral outline in the current image.

11. The interventional therapy system of claim 10, further comprising a rendering device, wherein the controller is further configured to render the current image with the selected peripheral outline superposed thereon using the rendering device.

12. A method for rendering a superposed image, the method performed by at least one controller of an interventional therapy system and comprising acts of:
obtaining a reference image dataset of an object of interest (OOI);
segmenting the reference image dataset to determine peripheral outlines of the OOI in the plurality image slices;
acquiring a current image of the OOI using an ultrasound probe;
selecting a peripheral outline of a selected image slice of the plurality of slices of the reference image dataset which is determined to correspond to the current image;
deformably registering the selected image slice of the plurality of slices of the reference image dataset with the current image to obtain at least one deformation vector;
and
applying the at least one deformation vector to the selected peripheral outline of the selected image slice selected from the reference image and corresponding to the current image to obtain a modified peripheral outline of the OOI in the selected image slice of the reference image dataset that represents a most current estimated peripheral outline by modifying the selected peripheral outline of the image slice of the plurality of slices of the reference image dataset in accordance with at least one deformation vector without using any peripheral outline in the current image.

13. The method of claim 12, further comprising an act of rendering, on a rendering device, the current image with the selected peripheral outline of the selected image slice of the plurality of slices of the reference image dataset superposed thereon.

14. The method of claim 12, further comprising an act of obtaining, from at least one sensor, location information comprising at least one of a position and an orientation of the ultrasound probe when the current image was acquired.

15. A non-transitory computer readable medium comprising computer instructions which, when executed by at least one processor, configure the at least one processor to control an interventional therapy system to render a superposed image, to perform acts of:
- obtaining a reference image dataset of an object of interest (OOI);
- segmenting the reference image dataset to determine peripheral outlines of the OOI in the plurality image slices;
- acquiring a current image of the OOI using an ultrasound probe;
- selecting a peripheral outline f a selected image slice of the plurality of slices of the reference image dataset which is determined to correspond to the current image;
- deformably registering the selected image slice of the plurality of slices of the reference image dataset with the current image to obtain at least one deformation vector;

and
- apply the at least one deformation vector to the selected peripheral outline of the selected image slice selected from the reference image and corresponding to the current image to obtain a modified peripheral outline of the OOI in the selected image slice of the reference image dataset that represents a most current estimated peripheral outline by modifying the selected peripheral outline of the image slice of the plurality of slices of the reference image dataset in accordance with at least one deformation vector without using any peripheral outline in the current image.

* * * * *